United States Patent [19]
Balazs et al.

[11] Patent Number: 5,514,547
[45] Date of Patent: May 7, 1996

[54] MOLECULAR GENETIC IDENTIFICATION USING PROBES THAT RECOGNIZE POLYMORPHIC LOCI

[75] Inventors: Ivan Balazs, New Rochelle, N.Y.; Zvi G. Loewy, Fair Lawn, N.J.; John Neuweiler, Brooklyn; Howard J. Baum, Stony Point, both of N.Y.; Vivian Ruvolo, Baltimore, Md.

[73] Assignee: Lifecodes Corporation, Stamford, Conn.

[21] Appl. No.: 192,233

[22] Filed: Feb. 4, 1994

(Under 37 CFR 1.47)

Related U.S. Application Data

[63] Continuation of Ser. No. 50,746, Apr. 21, 1993, abandoned, which is a continuation of Ser. No. 650,511, Feb. 5, 1991, abandoned.

[51] Int. Cl.$^6$ .............................. C07H 21/04; C12Q 1/68
[52] U.S. Cl. ........................... 435/6; 536/18.7; 536/23.1; 536/24.3; 935/77; 935/78
[58] Field of Search ............................... 435/6; 536/18.7, 536/23.1, 24.3; 935/77, 78

[56] References Cited

U.S. PATENT DOCUMENTS

| | | | |
|---|---|---|---|
| 4,683,195 | 7/1987 | Mullis et al. | 435/91 |
| 4,683,202 | 7/1987 | Mullis | 435/91 |
| 4,963,663 | 10/1990 | White et al. | 536/27 |

FOREIGN PATENT DOCUMENTS

| | | |
|---|---|---|
| 0349024 | 1/1994 | European Pat. Off. |

OTHER PUBLICATIONS

Lewontin, R. C., J. L. Hubby (1966) "Molecular Approach to the Study of Genic Heterozygosity in Natural Populations. II. Amount of Variation and Degree of Heterozygosity in Natural Populations of *Drosophila pseudoobscura*" Genetics 54:595–609.

Southern, E. M. (1975) "Detection of Specific Sequences Among DNA Fragments Separated by Gel Electrophoresis" J. Mol. Biol. 98:503–517.

Baird, M. et al. (1987) "The Application of DNA–Print for the Estimation of Paternity" Advances in Forensic Haemogenetics 2:354–358.

Baird, M. et al. (1987) "The Application of DNA–Print for Identification from Forensic Biological Materials" Advances in Forensic Haemogenetics 2:396–402.

Baird, M. et al. (1986) "Allele Frequency Distribution of Two Highly Polymorphic DNA Sequences in Three Ethnic Groups and Its Application to the Determination of Paternity" Am. J. Hum. Genet. 39:489–501.

Boerwinkle, E. et al. (1989) "Rapid typing of tandemly repeated hypervariable loci by the polymerase chain reaction: Application to the apolipoprotein B 3' hypervariable region" Proc. Natl. Acad. Sci. USA 86:212–216.

Horn, G. T., B. Richard, K. W. Klinger (1989) "Amplification of a highly polymorphic VNTR segment by the polymerase chain reaction" Nucleic Acids Research 17(5):2140.

Wu, S. S. Seino, G. I. Bell (1990) "Human collagen, type II, alpha 1, (COL2A1) gene: VNTR polymorphism detected by gene amplification" Nucleic Acids Research 18(10):3102.

Kasai, K., Y. Nakamura, R. White (1990) "Amplification of a Variable Number of Tandem Repeats (VNTR) Locus (pMCT118) by the Polymerase Chain Reaction (PCR) and Its Application to Forensic Science" J. Foren. Sci. 35:1196–1200.

Primary Examiner—W. Gary Jones
Assistant Examiner—Paul B. Tran
Attorney, Agent, or Firm—Saliwanchik & Saliwanchik

[57] ABSTRACT

Polynucleotide sequences and cloned DNA fragments useful for visualizing DNA polymorphism and other genetic analyses are disclosed herein. Specifically, polynucleotide probes and methods are employed to identify Variable Tandem Repeat (VTR) polymorphisms useful in paternity determination, forensics testing, disease diagnostics, cell line identification, ro chimerism/mosaicism determination as in distinguishing zygosity or following transplantation.

3 Claims, 14 Drawing Sheets

Figure 4A

| DNA FRAGMENT SIZE (Kb) | (PstI-DNA) BLACK | CAUCASIAN | CH.ORIENTAL FREQUENCY (%) | (HaeIII-DNA) BLACK | CAUCASIAN |
|---|---|---|---|---|---|
| 1.300 | 0.0000 | 0.0000 | 0.0000 | 0.0000 | 0.0018 |
| 1.307 | 0.0000 | 0.0000 | 0.0000 | 0.0000 | 0.0000 |
| 1.313 | 0.0000 | 0.0000 | 0.0000 | 0.0000 | 0.0000 |
| 1.320 | 0.0000 | 0.0000 | 0.0000 | 0.0000 | 0.0000 |
| 1.326 | 0.0000 | 0.0000 | 0.0000 | 0.0000 | 0.0000 |
| 1.333 | 0.0000 | 0.0000 | 0.0000 | 0.0000 | 0.0000 |
| 1.339 | 0.0000 | 0.0000 | 0.0000 | 0.0000 | 0.0000 |
| 1.346 | 0.0000 | 0.0000 | 0.0000 | 0.0000 | 0.0000 |
| 1.353 | 0.0000 | 0.0000 | 0.0000 | 0.0000 | 0.0000 |
| 1.360 | 0.0000 | 0.0000 | 0.0000 | 0.0000 | 0.0000 |
| 1.366 | 0.0000 | 0.0000 | 0.0000 | 0.0000 | 0.0000 |
| 1.373 | 0.0000 | 0.0000 | 0.0000 | 0.0000 | 0.0000 |
| 1.380 | 0.0000 | 0.0000 | 0.0000 | 0.0000 | 0.0000 |
| 1.387 | 0.0000 | 0.0000 | 0.0000 | 0.0000 | 0.0000 |
| 1.394 | 0.0000 | 0.0000 | 0.0000 | 0.0000 | 0.0000 |
| 1.401 | 0.0000 | 0.0000 | 0.0000 | 0.0000 | 0.0000 |
| 1.408 | 0.0000 | 0.0000 | 0.0000 | 0.0000 | 0.0000 |
| 1.415 | 0.0000 | 0.0000 | 0.0000 | 0.0000 | 0.0000 |
| 1.422 | 0.0000 | 0.0000 | 0.0000 | 0.0000 | 0.0000 |
| 1.429 | 0.0000 | 0.0000 | 0.0000 | 0.0000 | 0.0000 |
| 1.436 | 0.0000 | 0.0000 | 0.0000 | 0.0000 | 0.0000 |
| 1.444 | 0.0000 | 0.0000 | 0.0000 | 0.0000 | 0.0018 |
| 1.451 | 0.0000 | 0.0000 | 0.0000 | 0.0000 | 0.0000 |
| 1.458 | 0.0000 | 0.0000 | 0.0000 | 0.0000 | 0.0000 |
| 1.465 | 0.0000 | 0.0000 | 0.0000 | 0.0000 | 0.0000 |
| 1.473 | 0.0000 | 0.0000 | 0.0000 | 0.0000 | 0.0000 |
| 1.480 | 0.0000 | 0.0000 | 0.0000 | 0.0000 | 0.0000 |
| 1.487 | 0.0000 | 0.0000 | 0.0000 | 0.0000 | 0.0000 |
| 1.495 | 0.0000 | 0.0000 | 0.0000 | 0.0000 | 0.0000 |
| 1.502 | 0.0000 | 0.0000 | 0.0000 | 0.0000 | 0.0000 |
| 1.510 | 0.0000 | 0.0000 | 0.0000 | 0.0000 | 0.0000 |
| 1.517 | 0.0000 | 0.0000 | 0.0000 | 0.0000 | 0.0000 |
| 1.525 | 0.0000 | 0.0000 | 0.0000 | 0.0000 | 0.0000 |
| 1.533 | 0.0000 | 0.0000 | 0.0000 | 0.0000 | 0.0000 |
| 1.540 | 0.0000 | 0.0000 | 0.0000 | 0.0000 | 0.0000 |
| 1.548 | 0.0000 | 0.0000 | 0.0000 | 0.0000 | 0.0000 |
| 1.556 | 0.0000 | 0.0000 | 0.0000 | 0.0000 | 0.0000 |
| 1.563 | 0.0000 | 0.0000 | 0.0000 | 0.0000 | 0.0000 |
| 1.571 | 0.0000 | 0.0000 | 0.0000 | 0.0000 | 0.0000 |
| 1.579 | 0.0000 | 0.0000 | 0.0000 | 0.0000 | 0.0000 |
| 1.587 | 0.0000 | 0.0000 | 0.0000 | 0.0000 | 0.0000 |
| 1.595 | 0.0000 | 0.0000 | 0.0000 | 0.0000 | 0.0000 |
| 1.603 | 0.0000 | 0.0000 | 0.0000 | 0.0000 | 0.0000 |
| 1.611 | 0.0000 | 0.0000 | 0.0000 | 0.0000 | 0.0000 |
| 1.619 | 0.0000 | 0.0000 | 0.0000 | 0.0000 | 0.0000 |
| 1.627 | 0.0000 | 0.0000 | 0.0000 | 0.0000 | 0.0000 |
| 1.635 | 0.0000 | 0.0000 | 0.0000 | 0.0000 | 0.0000 |

Figure 4B

| | | | | | |
|---|---|---|---|---|---|
| 1.643 | 0.0000 | 0.0000 | 0.0000 | 0.0000 | 0.0000 |
| 1.652 | 0.0000 | 0.0000 | 0.0000 | 0.0022 | 0.0000 |
| 1.660 | 0.0000 | 0.0000 | 0.0000 | 0.0000 | 0.0000 |
| 1.668 | 0.0000 | 0.0000 | 0.0000 | 0.0000 | 0.0000 |
| 1.677 | 0.0000 | 0.0000 | 0.0000 | 0.0000 | 0.0000 |
| 1.685 | 0.0000 | 0.0000 | 0.0000 | 0.0000 | 0.0000 |
| 1.693 | 0.0000 | 0.0000 | 0.0000 | 0.0000 | 0.0018 |
| 1.702 | 0.0000 | 0.0000 | 0.0000 | 0.0000 | 0.0000 |
| 1.710 | 0.0000 | 0.0000 | 0.0000 | 0.0000 | 0.0000 |
| 1.719 | 0.0000 | 0.0000 | 0.0000 | 0.0000 | 0.0000 |
| 1.727 | 0.0000 | 0.0000 | 0.0000 | 0.0000 | 0.0000 |
| 1.736 | 0.0000 | 0.0000 | 0.0000 | 0.0022 | 0.0000 |
| 1.745 | 0.0000 | 0.0000 | 0.0000 | 0.0022 | 0.0018 |
| 1.754 | 0.0000 | 0.0000 | 0.0000 | 0.0000 | 0.0000 |
| 1.762 | 0.0000 | 0.0000 | 0.0000 | 0.0000 | 0.0000 |
| 1.771 | 0.0000 | 0.0000 | 0.0000 | 0.0000 | 0.0018 |
| 1.780 | 0.0000 | 0.0000 | 0.0000 | 0.0000 | 0.0000 |
| 1.789 | 0.0000 | 0.0000 | 0.0000 | 0.0000 | 0.0000 |
| 1.798 | 0.0000 | 0.0000 | 0.0000 | 0.0000 | 0.0018 |
| 1.807 | 0.0000 | 0.0000 | 0.0000 | 0.0000 | 0.0000 |
| 1.816 | 0.0000 | 0.0000 | 0.0000 | 0.0000 | 0.0000 |
| 1.825 | 0.0000 | 0.0000 | 0.0000 | 0.0000 | 0.0000 |
| 1.834 | 0.0000 | 0.0000 | 0.0000 | 0.0000 | 0.0000 |
| 1.843 | 0.0000 | 0.0000 | 0.0000 | 0.0000 | 0.0000 |
| 1.852 | 0.0000 | 0.0000 | 0.0000 | 0.0000 | 0.0000 |
| 1.862 | 0.0000 | 0.0000 | 0.0000 | 0.0022 | 0.0000 |
| 1.871 | 0.0000 | 0.0000 | 0.0000 | 0.0000 | 0.0000 |
| 1.880 | 0.0000 | 0.0000 | 0.0000 | 0.0000 | 0.0000 |
| 1.890 | 0.0000 | 0.0000 | 0.0000 | 0.0000 | 0.0000 |
| 1.899 | 0.0000 | 0.0000 | 0.0000 | 0.0000 | 0.0018 |
| 1.909 | 0.0000 | 0.0000 | 0.0000 | 0.0000 | 0.0000 |
| 1.918 | 0.0000 | 0.0000 | 0.0000 | 0.0000 | 0.0000 |
| 1.928 | 0.0000 | 0.0000 | 0.0000 | 0.0000 | 0.0000 |
| 1.937 | 0.0000 | 0.0000 | 0.0000 | 0.0000 | 0.0000 |
| 1.947 | 0.0000 | 0.0000 | 0.0000 | 0.0000 | 0.0000 |
| 1.957 | 0.0000 | 0.0000 | 0.0000 | 0.0000 | 0.0000 |
| 1.967 | 0.0000 | 0.0000 | 0.0000 | 0.0022 | 0.0000 |
| 1.976 | 0.0000 | 0.0000 | 0.0000 | 0.0000 | 0.0000 |
| 1.986 | 0.0000 | 0.0000 | 0.0000 | 0.0022 | 0.0018 |
| 1.996 | 0.0000 | 0.0000 | 0.0000 | 0.0043 | 0.0000 |
| 2.006 | 0.0000 | 0.0000 | 0.0000 | 0.0022 | 0.0018 |
| 2.016 | 0.0000 | 0.0000 | 0.0000 | 0.0000 | 0.0000 |
| 2.026 | 0.0000 | 0.0000 | 0.0000 | 0.0043 | 0.0000 |
| 2.037 | 0.0000 | 0.0000 | 0.0000 | 0.0022 | 0.0018 |
| 2.047 | 0.0000 | 0.0000 | 0.0000 | 0.0022 | 0.0000 |
| 2.057 | 0.0000 | 0.0000 | 0.0000 | 0.0043 | 0.0000 |
| 2.067 | 0.0000 | 0.0000 | 0.0000 | 0.0043 | 0.0000 |
| 2.078 | 0.0000 | 0.0000 | 0.0000 | 0.0022 | 0.0037 |
| 2.088 | 0.0000 | 0.0000 | 0.0000 | 0.0022 | 0.0037 |
| 2.098 | 0.0000 | 0.0000 | 0.0000 | 0.0043 | 0.0074 |
| 2.109 | 0.0000 | 0.0000 | 0.0000 | 0.0043 | 0.0055 |
| 2.119 | 0.0000 | 0.0000 | 0.0000 | 0.0022 | 0.0037 |
| 2.130 | 0.0000 | 0.0000 | 0.0000 | 0.0065 | 0.0037 |
| 2.141 | 0.0000 | 0.0000 | 0.0000 | 0.0000 | 0.0000 |

Figure 4C

| | | | | | |
|---|---|---|---|---|---|
| 2.151 | 0.0000 | 0.0000 | 0.0000 | 0.0022 | 0.0000 |
| 2.162 | 0.0000 | 0.0000 | 0.0000 | 0.0000 | 0.0000 |
| 2.173 | 0.0000 | 0.0000 | 0.0000 | 0.0000 | 0.0000 |
| 2.184 | 0.0000 | 0.0000 | 0.0000 | 0.0000 | 0.0018 |
| 2.195 | 0.0000 | 0.0000 | 0.0000 | 0.0000 | 0.0018 |
| 2.206 | 0.0000 | 0.0000 | 0.0000 | 0.0000 | 0.0037 |
| 2.217 | 0.0000 | 0.0000 | 0.0000 | 0.0000 | 0.0018 |
| 2.228 | 0.0000 | 0.0000 | 0.0000 | 0.0000 | 0.0018 |
| 2.239 | 0.0000 | 0.0000 | 0.0000 | 0.0022 | 0.0018 |
| 2.250 | 0.0000 | 0.0000 | 0.0000 | 0.0000 | 0.0074 |
| 2.261 | 0.0000 | 0.0000 | 0.0000 | 0.0000 | 0.0000 |
| 2.273 | 0.0000 | 0.0000 | 0.0000 | 0.0022 | 0.0000 |
| 2.284 | 0.0000 | 0.0000 | 0.0000 | 0.0000 | 0.0055 |
| 2.295 | 0.0000 | 0.0000 | 0.0000 | 0.0000 | 0.0000 |
| 2.307 | 0.0000 | 0.0000 | 0.0000 | 0.0000 | 0.0000 |
| 2.318 | 0.0000 | 0.0000 | 0.0000 | 0.0022 | 0.0074 |
| 2.330 | 0.0000 | 0.0000 | 0.0000 | 0.0022 | 0.0111 |
| 2.342 | 0.0000 | 0.0000 | 0.0000 | 0.0043 | 0.0018 |
| 2.353 | 0.0000 | 0.0000 | 0.0000 | 0.0000 | 0.0018 |
| 2.365 | 0.0000 | 0.0000 | 0.0000 | 0.0000 | 0.0000 |
| 2.377 | 0.0000 | 0.0000 | 0.0000 | 0.0022 | 0.0074 |
| 2.389 | 0.0000 | 0.0000 | 0.0000 | 0.0000 | 0.0018 |
| 2.401 | 0.0000 | 0.0000 | 0.0000 | 0.0022 | 0.0000 |
| 2.413 | 0.0000 | 0.0000 | 0.0000 | 0.0000 | 0.0018 |
| 2.425 | 0.0000 | 0.0000 | 0.0000 | 0.0000 | 0.0037 |
| 2.437 | 0.0000 | 0.0000 | 0.0000 | 0.0000 | 0.0000 |
| 2.449 | 0.0000 | 0.0000 | 0.0000 | 0.0000 | 0.0000 |
| 2.461 | 0.0000 | 0.0000 | 0.0000 | 0.0000 | 0.0000 |
| 2.474 | 0.0000 | 0.0000 | 0.0000 | 0.0000 | 0.0000 |
| 2.486 | 0.0000 | 0.0000 | 0.0000 | 0.0000 | 0.0000 |
| 2.499 | 0.0000 | 0.0000 | 0.0000 | 0.0000 | 0.0000 |
| 2.511 | 0.0000 | 0.0000 | 0.0000 | 0.0000 | 0.0000 |
| 2.524 | 0.0000 | 0.0000 | 0.0000 | 0.0000 | 0.0000 |
| 2.536 | 0.0000 | 0.0000 | 0.0000 | 0.0022 | 0.0018 |
| 2.549 | 0.0000 | 0.0000 | 0.0000 | 0.0000 | 0.0018 |
| 2.562 | 0.0000 | 0.0000 | 0.0000 | 0.0043 | 0.0018 |
| 2.575 | 0.0000 | 0.0000 | 0.0000 | 0.0022 | 0.0000 |
| 2.587 | 0.0000 | 0.0000 | 0.0000 | 0.0065 | 0.0018 |
| 2.600 | 0.0000 | 0.0000 | 0.0000 | 0.0022 | 0.0000 |
| 2.613 | 0.0000 | 0.0000 | 0.0000 | 0.0022 | 0.0000 |
| 2.626 | 0.0000 | 0.0000 | 0.0000 | 0.0022 | 0.0018 |
| 2.640 | 0.0000 | 0.0000 | 0.0000 | 0.0022 | 0.0018 |
| 2.653 | 0.0000 | 0.0000 | 0.0000 | 0.0087 | 0.0018 |
| 2.666 | 0.0000 | 0.0000 | 0.0000 | 0.0000 | 0.0037 |
| 2.679 | 0.0000 | 0.0000 | 0.0000 | 0.0022 | 0.0000 |
| 2.693 | 0.0000 | 0.0000 | 0.0000 | 0.0043 | 0.0018 |
| 2.706 | 0.0000 | 0.0000 | 0.0000 | 0.0000 | 0.0000 |
| 2.720 | 0.0000 | 0.0000 | 0.0000 | 0.0000 | 0.0000 |
| 2.733 | 0.0000 | 0.0000 | 0.0000 | 0.0195 | 0.0018 |
| 2.747 | 0.0000 | 0.0000 | 0.0000 | 0.0022 | 0.0000 |
| 2.761 | 0.0000 | 0.0000 | 0.0000 | 0.0000 | 0.0037 |
| 2.775 | 0.0000 | 0.0000 | 0.0000 | 0.0043 | 0.0000 |
| 2.788 | 0.0000 | 0.0000 | 0.0000 | 0.0043 | 0.0000 |
| 2.802 | 0.0000 | 0.0000 | 0.0000 | 0.0000 | 0.0000 |

Figure 4D

| | | | | | |
|---|---|---|---|---|---|
| 2.816 | 0.0000 | 0.0000 | 0.0000 | 0.0022 | 0.0000 |
| 2.830 | 0.0000 | 0.0000 | 0.0000 | 0.0000 | 0.0018 |
| 2.845 | 0.0000 | 0.0000 | 0.0000 | 0.0022 | 0.0000 |
| 2.859 | 0.0000 | 0.0000 | 0.0000 | 0.0000 | 0.0018 |
| 2.873 | 0.0000 | 0.0000 | 0.0000 | 0.0000 | 0.0000 |
| 2.887 | 0.0000 | 0.0000 | 0.0000 | 0.0000 | 0.0000 |
| 2.902 | 0.0000 | 0.0000 | 0.0000 | 0.0043 | 0.0037 |
| 2.916 | 0.0000 | 0.0000 | 0.0000 | 0.0000 | 0.0000 |
| 2.931 | 0.0000 | 0.0000 | 0.0000 | 0.0000 | 0.0018 |
| 2.946 | 0.0000 | 0.0000 | 0.0000 | 0.0022 | 0.0000 |
| 2.960 | 0.0000 | 0.0000 | 0.0000 | 0.0022 | 0.0000 |
| 2.975 | 0.0000 | 0.0000 | 0.0000 | 0.0043 | 0.0000 |
| 2.990 | 0.0000 | 0.0000 | 0.0000 | 0.0022 | 0.0000 |
| 3.005 | 0.0000 | 0.0000 | 0.0000 | 0.0000 | 0.0000 |
| 3.020 | 0.0000 | 0.0000 | 0.0000 | 0.0000 | 0.0037 |
| 3.035 | 0.0000 | 0.0000 | 0.0000 | 0.0000 | 0.0000 |
| 3.050 | 0.0000 | 0.0000 | 0.0000 | 0.0000 | 0.0037 |
| 3.066 | 0.0000 | 0.0000 | 0.0000 | 0.0000 | 0.0018 |
| 3.081 | 0.0000 | 0.0000 | 0.0000 | 0.0000 | 0.0000 |
| 3.096 | 0.0000 | 0.0000 | 0.0000 | 0.0000 | 0.0000 |
| 3.112 | 0.0000 | 0.0000 | 0.0000 | 0.0000 | 0.0018 |
| 3.127 | 0.0000 | 0.0000 | 0.0000 | 0.0000 | 0.0018 |
| 3.143 | 0.0000 | 0.0000 | 0.0000 | 0.0022 | 0.0037 |
| 3.159 | 0.0000 | 0.0000 | 0.0000 | 0.0022 | 0.0000 |
| 3.174 | 0.0000 | 0.0000 | 0.0000 | 0.0000 | 0.0055 |
| 3.190 | 0.0000 | 0.0000 | 0.0000 | 0.0000 | 0.0037 |
| 3.206 | 0.0000 | 0.0000 | 0.0000 | 0.0022 | 0.0000 |
| 3.222 | 0.0000 | 0.0000 | 0.0000 | 0.0000 | 0.0000 |
| 3.238 | 0.0000 | 0.0000 | 0.0000 | 0.0000 | 0.0037 |
| 3.255 | 0.0000 | 0.0000 | 0.0000 | 0.0022 | 0.0000 |
| 3.271 | 0.0000 | 0.0000 | 0.0000 | 0.0065 | 0.0055 |
| 3.287 | 0.0000 | 0.0000 | 0.0000 | 0.0022 | 0.0018 |
| 3.304 | 0.0000 | 0.0000 | 0.0000 | 0.0065 | 0.0018 |
| 3.320 | 0.0000 | 0.0000 | 0.0000 | 0.0000 | 0.0018 |
| 3.337 | 0.0000 | 0.0000 | 0.0000 | 0.0022 | 0.0018 |
| 3.353 | 0.0000 | 0.0000 | 0.0000 | 0.0065 | 0.0000 |
| 3.370 | 0.0000 | 0.0000 | 0.0000 | 0.0130 | 0.0000 |
| 3.387 | 0.0000 | 0.0000 | 0.0000 | 0.0087 | 0.0000 |
| 3.404 | 0.0000 | 0.0000 | 0.0000 | 0.0043 | 0.0037 |
| 3.421 | 0.0000 | 0.0000 | 0.0000 | 0.0043 | 0.0018 |
| 3.438 | 0.0000 | 0.0000 | 0.0000 | 0.0022 | 0.0000 |
| 3.455 | 0.0000 | 0.0000 | 0.0000 | 0.0022 | 0.0000 |
| 3.473 | 0.0000 | 0.0000 | 0.0000 | 0.0130 | 0.0018 |
| 3.490 | 0.0000 | 0.0000 | 0.0000 | 0.0022 | 0.0018 |
| 3.507 | 0.0000 | 0.0000 | 0.0000 | 0.0108 | 0.0018 |
| 3.525 | 0.0000 | 0.0000 | 0.0000 | 0.0000 | 0.0000 |
| 3.543 | 0.0000 | 0.0000 | 0.0000 | 0.0043 | 0.0018 |
| 3.560 | 0.0000 | 0.0000 | 0.0000 | 0.0065 | 0.0000 |
| 3.578 | 0.0000 | 0.0000 | 0.0000 | 0.0022 | 0.0018 |
| 3.596 | 0.0037 | 0.0000 | 0.0000 | 0.0087 | 0.0037 |
| 3.614 | 0.0018 | 0.0000 | 0.0000 | 0.0043 | 0.0000 |
| 3.632 | 0.0018 | 0.0000 | 0.0000 | 0.0043 | 0.0000 |
| 3.650 | 0.0037 | 0.0000 | 0.0000 | 0.0065 | 0.0000 |
| 3.668 | 0.0000 | 0.0000 | 0.0000 | 0.0065 | 0.0018 |

Figure 4E

| | | | | | |
|---|---|---|---|---|---|
| 3.687 | 0.0018 | 0.0000 | 0.0000 | 0.0065 | 0.0018 |
| 3.705 | 0.0000 | 0.0000 | 0.0000 | 0.0043 | 0.0000 |
| 3.724 | 0.0000 | 0.0000 | 0.0000 | 0.0065 | 0.0000 |
| 3.742 | 0.0000 | 0.0000 | 0.0000 | 0.0065 | 0.0000 |
| 3.761 | 0.0000 | 0.0000 | 0.0000 | 0.0065 | 0.0037 |
| 3.780 | 0.0000 | 0.0000 | 0.0000 | 0.0043 | 0.0074 |
| 3.799 | 0.0000 | 0.0000 | 0.0000 | 0.0043 | 0.0018 |
| 3.818 | 0.0000 | 0.0000 | 0.0000 | 0.0065 | 0.0074 |
| 3.837 | 0.0000 | 0.0000 | 0.0000 | 0.0108 | 0.0055 |
| 3.856 | 0.0000 | 0.0000 | 0.0000 | 0.0022 | 0.0018 |
| 3.875 | 0.0000 | 0.0000 | 0.0000 | 0.0130 | 0.0000 |
| 3.895 | 0.0000 | 0.0000 | 0.0000 | 0.0130 | 0.0018 |
| 3.914 | 0.0000 | 0.0000 | 0.0000 | 0.0238 | 0.0055 |
| 3.934 | 0.0000 | 0.0000 | 0.0000 | 0.0152 | 0.0074 |
| 3.953 | 0.0000 | 0.0000 | 0.0000 | 0.0065 | 0.0037 |
| 3.973 | 0.0000 | 0.0000 | 0.0000 | 0.0087 | 0.0000 |
| 3.993 | 0.0000 | 0.0000 | 0.0000 | 0.0087 | 0.0074 |
| 4.013 | 0.0000 | 0.0000 | 0.0000 | 0.0238 | 0.0129 |
| 4.033 | 0.0000 | 0.0000 | 0.0000 | 0.0043 | 0.0055 |
| 4.053 | 0.0000 | 0.0000 | 0.0000 | 0.0022 | 0.0074 |
| 4.074 | 0.0000 | 0.0000 | 0.0000 | 0.0108 | 0.0074 |
| 4.094 | 0.0000 | 0.0000 | 0.0000 | 0.0065 | 0.0037 |
| 4.114 | 0.0000 | 0.0000 | 0.0000 | 0.0043 | 0.0055 |
| 4.135 | 0.0000 | 0.0000 | 0.0000 | 0.0043 | 0.0111 |
| 4.156 | 0.0000 | 0.0000 | 0.0000 | 0.0043 | 0.0074 |
| 4.176 | 0.0000 | 0.0000 | 0.0000 | 0.0108 | 0.0111 |
| 4.197 | 0.0000 | 0.0000 | 0.0000 | 0.0065 | 0.0166 |
| 4.218 | 0.0000 | 0.0000 | 0.0000 | 0.0065 | 0.0148 |
| 4.239 | 0.0000 | 0.0000 | 0.0000 | 0.0065 | 0.0166 |
| 4.261 | 0.0000 | 0.0000 | 0.0000 | 0.0152 | 0.0037 |
| 4.282 | 0.0000 | 0.0000 | 0.0000 | 0.0022 | 0.0074 |
| 4.303 | 0.0000 | 0.0000 | 0.0000 | 0.0043 | 0.0037 |
| 4.325 | 0.0018 | 0.0000 | 0.0000 | 0.0022 | 0.0092 |
| 4.346 | 0.0000 | 0.0000 | 0.0000 | 0.0000 | 0.0018 |
| 4.368 | 0.0000 | 0.0000 | 0.0000 | 0.0043 | 0.0055 |
| 4.390 | 0.0000 | 0.0000 | 0.0000 | 0.0043 | 0.0092 |
| 4.412 | 0.0000 | 0.0000 | 0.0000 | 0.0065 | 0.0295 |
| 4.434 | 0.0000 | 0.0000 | 0.0000 | 0.0043 | 0.0111 |
| 4.456 | 0.0000 | 0.0000 | 0.0000 | 0.0000 | 0.0111 |
| 4.478 | 0.0000 | 0.0000 | 0.0000 | 0.0087 | 0.0258 |
| 4.501 | 0.0000 | 0.0000 | 0.0000 | 0.0216 | 0.0203 |
| 4.523 | 0.0000 | 0.0000 | 0.0000 | 0.0043 | 0.0221 |
| 4.546 | 0.0000 | 0.0000 | 0.0000 | 0.0087 | 0.0111 |
| 4.569 | 0.0000 | 0.0000 | 0.0000 | 0.0022 | 0.0074 |
| 4.592 | 0.0000 | 0.0000 | 0.0000 | 0.0195 | 0.0240 |
| 4.614 | 0.0000 | 0.0000 | 0.0000 | 0.0022 | 0.0129 |
| 4.638 | 0.0000 | 0.0000 | 0.0000 | 0.0043 | 0.0092 |
| 4.661 | 0.0000 | 0.0000 | 0.0000 | 0.0043 | 0.0111 |
| 4.684 | 0.0000 | 0.0000 | 0.0000 | 0.0000 | 0.0055 |
| 4.707 | 0.0000 | 0.0000 | 0.0000 | 0.0022 | 0.0018 |
| 4.731 | 0.0000 | 0.0000 | 0.0000 | 0.0022 | 0.0000 |
| 4.755 | 0.0000 | 0.0000 | 0.0000 | 0.0065 | 0.0055 |
| 4.778 | 0.0000 | 0.0000 | 0.0000 | 0.0043 | 0.0074 |
| 4.802 | 0.0000 | 0.0000 | 0.0000 | 0.0043 | 0.0129 |

Figure 4F

| | | | | | |
|---|---|---|---|---|---|
| 4.826 | 0.0000 | 0.0000 | 0.0000 | 0.0173 | 0.0037 |
| 4.850 | 0.0000 | 0.0000 | 0.0000 | 0.0087 | 0.0166 |
| 4.875 | 0.0000 | 0.0000 | 0.0000 | 0.0043 | 0.0037 |
| 4.899 | 0.0000 | 0.0000 | 0.0000 | 0.0043 | 0.0000 |
| 4.924 | 0.0000 | 0.0000 | 0.0000 | 0.0087 | 0.0037 |
| 4.948 | 0.0000 | 0.0000 | 0.0000 | 0.0065 | 0.0018 |
| 4.973 | 0.0000 | 0.0000 | 0.0000 | 0.0043 | 0.0111 |
| 4.998 | 0.0000 | 0.0000 | 0.0000 | 0.0087 | 0.0018 |
| 5.023 | 0.0000 | 0.0000 | 0.0000 | 0.0022 | 0.0018 |
| 5.048 | 0.0000 | 0.0000 | 0.0000 | 0.0000 | 0.0000 |
| 5.073 | 0.0000 | 0.0018 | 0.0000 | 0.0043 | 0.0055 |
| 5.099 | 0.0000 | 0.0000 | 0.0000 | 0.0043 | 0.0037 |
| 5.124 | 0.0000 | 0.0000 | 0.0000 | 0.0065 | 0.0018 |
| 5.150 | 0.0000 | 0.0000 | 0.0000 | 0.0000 | 0.0037 |
| 5.175 | 0.0000 | 0.0000 | 0.0000 | 0.0043 | 0.0018 |
| 5.201 | 0.0000 | 0.0000 | 0.0055 | 0.0043 | 0.0000 |
| 5.227 | 0.0000 | 0.0009 | 0.0027 | 0.0000 | 0.0000 |
| 5.253 | 0.0000 | 0.0000 | 0.0000 | 0.0000 | 0.0018 |
| 5.280 | 0.0000 | 0.0009 | 0.0000 | 0.0000 | 0.0000 |
| 5.306 | 0.0000 | 0.0000 | 0.0000 | 0.0022 | 0.0000 |
| 5.333 | 0.0000 | 0.0000 | 0.0000 | 0.0000 | 0.0018 |
| 5.359 | 0.0000 | 0.0000 | 0.0000 | 0.0000 | 0.0000 |
| 5.386 | 0.0000 | 0.0000 | 0.0000 | 0.0022 | 0.0000 |
| 5.413 | 0.0000 | 0.0000 | 0.0000 | 0.0000 | 0.0000 |
| 5.440 | 0.0000 | 0.0009 | 0.0000 | 0.0000 | 0.0055 |
| 5.467 | 0.0018 | 0.0027 | 0.0000 | 0.0022 | 0.0018 |
| 5.495 | 0.0018 | 0.0000 | 0.0000 | 0.0065 | 0.0037 |
| 5.522 | 0.0000 | 0.0000 | 0.0000 | 0.0043 | 0.0000 |
| 5.550 | 0.0018 | 0.0018 | 0.0000 | 0.0000 | 0.0037 |
| 5.577 | 0.0000 | 0.0000 | 0.0000 | 0.0022 | 0.0018 |
| 5.605 | 0.0000 | 0.0000 | 0.0027 | 0.0000 | 0.0018 |
| 5.633 | 0.0000 | 0.0009 | 0.0000 | 0.0000 | 0.0018 |
| 5.662 | 0.0018 | 0.0009 | 0.0000 | 0.0000 | 0.0092 |
| 5.690 | 0.0018 | 0.0009 | 0.0000 | 0.0000 | 0.0000 |
| 5.718 | 0.0000 | 0.0000 | 0.0000 | 0.0065 | 0.0018 |
| 5.747 | 0.0018 | 0.0027 | 0.0000 | 0.0000 | 0.0037 |
| 5.776 | 0.0018 | 0.0018 | 0.0000 | 0.0000 | 0.0055 |
| 5.804 | 0.0037 | 0.0046 | 0.0000 | 0.0000 | 0.0037 |
| 5.833 | 0.0037 | 0.0009 | 0.0000 | 0.0000 | 0.0111 |
| 5.863 | 0.0000 | 0.0055 | 0.0000 | 0.0000 | 0.0018 |
| 5.892 | 0.0055 | 0.0055 | 0.0000 | 0.0043 | 0.0037 |
| 5.921 | 0.0018 | 0.0073 | 0.0000 | 0.0000 | 0.0018 |
| 5.951 | 0.0037 | 0.0073 | 0.0000 | 0.0043 | 0.0037 |
| 5.981 | 0.0037 | 0.0037 | 0.0000 | 0.0043 | 0.0000 |
| 6.011 | 0.0037 | 0.0027 | 0.0000 | 0.0022 | 0.0000 |
| 6.041 | 0.0037 | 0.0073 | 0.0000 | 0.0000 | 0.0000 |
| 6.071 | 0.0037 | 0.0027 | 0.0000 | 0.0000 | 0.0000 |
| 6.101 | 0.0018 | 0.0073 | 0.0000 | 0.0000 | 0.0037 |
| 6.132 | 0.0000 | 0.0082 | 0.0000 | 0.0000 | 0.0018 |
| 6.162 | 0.0018 | 0.0082 | 0.0055 | 0.0000 | 0.0000 |
| 6.193 | 0.0018 | 0.0055 | 0.0027 | 0.0022 | 0.0037 |
| 6.224 | 0.0018 | 0.0027 | 0.0000 | 0.0022 | 0.0018 |
| 6.255 | 0.0000 | 0.0018 | 0.0000 | 0.0022 | 0.0018 |
| 6.287 | 0.0037 | 0.0018 | 0.0000 | 0.0022 | 0.0018 |

Figure 4G

| | | | | | |
|---|---|---|---|---|---|
| 6.318 | 0.0055 | 0.0064 | 0.0000 | 0.0043 | 0.0055 |
| 6.350 | 0.0037 | 0.0073 | 0.0027 | 0.0000 | 0.0000 |
| 6.381 | 0.0165 | 0.0055 | 0.0027 | 0.0022 | 0.0000 |
| 6.413 | 0.0037 | 0.0064 | 0.0000 | 0.0000 | 0.0018 |
| 6.445 | 0.0037 | 0.0027 | 0.0082 | 0.0000 | 0.0000 |
| 6.478 | 0.0018 | 0.0037 | 0.0082 | 0.0022 | 0.0037 |
| 6.510 | 0.0037 | 0.0046 | 0.0082 | 0.0000 | 0.0018 |
| 6.543 | 0.0092 | 0.0027 | 0.0000 | 0.0000 | 0.0000 |
| 6.575 | 0.0018 | 0.0037 | 0.0055 | 0.0000 | 0.0037 |
| 6.608 | 0.0073 | 0.0018 | 0.0027 | 0.0022 | 0.0000 |
| 6.641 | 0.0092 | 0.0055 | 0.0055 | 0.0000 | 0.0000 |
| 6.674 | 0.0073 | 0.0009 | 0.0137 | 0.0000 | 0.0000 |
| 6.708 | 0.0055 | 0.0018 | 0.0027 | 0.0000 | 0.0000 |
| 6.741 | 0.0018 | 0.0037 | 0.0027 | 0.0022 | 0.0055 |
| 6.775 | 0.0037 | 0.0037 | 0.0055 | 0.0000 | 0.0018 |
| 6.809 | 0.0055 | 0.0073 | 0.0164 | 0.0000 | 0.0037 |
| 6.843 | 0.0092 | 0.0137 | 0.0082 | 0.0000 | 0.0018 |
| 6.877 | 0.0055 | 0.0046 | 0.0246 | 0.0000 | 0.0018 |
| 6.912 | 0.0037 | 0.0073 | 0.0328 | 0.0000 | 0.0037 |
| 6.946 | 0.0073 | 0.0082 | 0.0137 | 0.0043 | 0.0037 |
| 6.981 | 0.0110 | 0.0101 | 0.0164 | 0.0000 | 0.0037 |
| 7.016 | 0.0073 | 0.0128 | 0.0164 | 0.0022 | 0.0000 |
| 7.051 | 0.0073 | 0.0101 | 0.0055 | 0.0000 | 0.0000 |
| 7.086 | 0.0110 | 0.0137 | 0.0082 | 0.0000 | 0.0000 |
| 7.121 | 0.0275 | 0.0174 | 0.0164 | 0.0000 | 0.0037 |
| 7.157 | 0.0092 | 0.0101 | 0.0109 | 0.0000 | 0.0092 |
| 7.193 | 0.0201 | 0.0046 | 0.0082 | 0.0000 | 0.0018 |
| 7.229 | 0.0183 | 0.0110 | 0.0055 | 0.0022 | 0.0037 |
| 7.265 | 0.0128 | 0.0037 | 0.0055 | 0.0000 | 0.0018 |
| 7.301 | 0.0165 | 0.0037 | 0.0055 | 0.0043 | 0.0055 |
| 7.338 | 0.0147 | 0.0055 | 0.0055 | 0.0000 | 0.0018 |
| 7.375 | 0.0165 | 0.0055 | 0.0109 | 0.0000 | 0.0018 |
| 7.411 | 0.0183 | 0.0046 | 0.0027 | 0.0022 | 0.0018 |
| 7.448 | 0.0073 | 0.0064 | 0.0027 | 0.0000 | 0.0018 |
| 7.486 | 0.0201 | 0.0119 | 0.0055 | 0.0000 | 0.0037 |
| 7.523 | 0.0073 | 0.0046 | 0.0055 | 0.0022 | 0.0000 |
| 7.561 | 0.0220 | 0.0037 | 0.0191 | 0.0000 | 0.0037 |
| 7.599 | 0.0220 | 0.0037 | 0.0109 | 0.0000 | 0.0074 |
| 7.637 | 0.0330 | 0.0055 | 0.0164 | 0.0022 | 0.0074 |
| 7.675 | 0.0256 | 0.0037 | 0.0301 | 0.0000 | 0.0055 |
| 7.713 | 0.0275 | 0.0092 | 0.0246 | 0.0000 | 0.0000 |
| 7.752 | 0.0238 | 0.0092 | 0.0301 | 0.0000 | 0.0018 |
| 7.790 | 0.0037 | 0.0037 | 0.0137 | 0.0000 | 0.0018 |
| 7.829 | 0.0128 | 0.0101 | 0.0164 | 0.0000 | 0.0000 |
| 7.868 | 0.0092 | 0.0110 | 0.0301 | 0.0000 | 0.0037 |
| 7.908 | 0.0073 | 0.0128 | 0.0191 | 0.0043 | 0.0018 |
| 7.947 | 0.0128 | 0.0137 | 0.0000 | 0.0000 | 0.0037 |
| 7.987 | 0.0165 | 0.0220 | 0.0164 | 0.0000 | 0.0018 |
| 8.027 | 0.0073 | 0.0247 | 0.0164 | 0.0000 | 0.0000 |
| 8.067 | 0.0147 | 0.0137 | 0.0164 | 0.0000 | 0.0092 |
| 8.108 | 0.0110 | 0.0128 | 0.0027 | 0.0022 | 0.0018 |
| 8.148 | 0.0128 | 0.0201 | 0.0055 | 0.0000 | 0.0055 |
| 8.189 | 0.0073 | 0.0201 | 0.0164 | 0.0022 | 0.0037 |
| 8.230 | 0.0110 | 0.0385 | 0.0109 | 0.0022 | 0.0018 |

Figure 4H

| | | | | | |
|---|---|---|---|---|---|
| 8.271 | 0.0183 | 0.0375 | 0.0164 | 0.0043 | 0.0055 |
| 8.312 | 0.0183 | 0.0247 | 0.0273 | 0.0000 | 0.0018 |
| 8.354 | 0.0073 | 0.0220 | 0.0328 | 0.0000 | 0.0018 |
| 8.396 | 0.0055 | 0.0137 | 0.0246 | 0.0043 | 0.0055 |
| 8.438 | 0.0055 | 0.0165 | 0.0109 | 0.0000 | 0.0018 |
| 8.480 | 0.0073 | 0.0119 | 0.0137 | 0.0043 | 0.0018 |
| 8.522 | 0.0092 | 0.0064 | 0.0219 | 0.0000 | 0.0018 |
| 8.565 | 0.0128 | 0.0046 | 0.0137 | 0.0022 | 0.0000 |
| 8.608 | 0.0055 | 0.0037 | 0.0191 | 0.0043 | 0.0037 |
| 8.651 | 0.0110 | 0.0037 | 0.0301 | 0.0022 | 0.0018 |
| 8.694 | 0.0018 | 0.0018 | 0.0137 | 0.0000 | 0.0018 |
| 8.737 | 0.0037 | 0.0018 | 0.0164 | 0.0022 | 0.0018 |
| 8.781 | 0.0000 | 0.0046 | 0.0000 | 0.0000 | 0.0000 |
| 8.825 | 0.0037 | 0.0018 | 0.0027 | 0.0000 | 0.0000 |
| 8.869 | 0.0037 | 0.0018 | 0.0027 | 0.0022 | 0.0000 |
| 8.913 | 0.0018 | 0.0064 | 0.0055 | 0.0000 | 0.0000 |
| 8.958 | 0.0000 | 0.0009 | 0.0027 | 0.0022 | 0.0037 |
| 9.003 | 0.0037 | 0.0009 | 0.0000 | 0.0000 | 0.0018 |
| 9.048 | 0.0000 | 0.0000 | 0.0055 | 0.0000 | 0.0000 |
| 9.093 | 0.0000 | 0.0000 | 0.0055 | 0.0108 | 0.0018 |
| 9.138 | 0.0018 | 0.0018 | 0.0000 | 0.0000 | 0.0000 |
| 9.184 | 0.0037 | 0.0073 | 0.0055 | 0.0000 | 0.0000 |
| 9.230 | 0.0000 | 0.0064 | 0.0027 | 0.0043 | 0.0000 |
| 9.276 | 0.0018 | 0.0037 | 0.0027 | 0.0000 | 0.0018 |
| 9.323 | 0.0000 | 0.0073 | 0.0082 | 0.0000 | 0.0000 |
| 9.369 | 0.0018 | 0.0082 | 0.0000 | 0.0000 | 0.0000 |
| 9.416 | 0.0000 | 0.0055 | 0.0027 | 0.0043 | 0.0000 |
| 9.463 | 0.0018 | 0.0055 | 0.0000 | 0.0000 | 0.0000 |
| 9.510 | 0.0018 | 0.0064 | 0.0055 | 0.0000 | 0.0000 |
| 9.558 | 0.0018 | 0.0037 | 0.0000 | 0.0000 | 0.0000 |
| 9.606 | 0.0000 | 0.0046 | 0.0055 | 0.0000 | 0.0000 |
| 9.654 | 0.0018 | 0.0037 | 0.0000 | 0.0000 | 0.0000 |
| 9.702 | 0.0037 | 0.0018 | 0.0027 | 0.0022 | 0.0000 |
| 9.751 | 0.0000 | 0.0018 | 0.0000 | 0.0000 | 0.0000 |
| 9.799 | 0.0000 | 0.0018 | 0.0055 | 0.0022 | 0.0000 |
| 9.848 | 0.0000 | 0.0046 | 0.0027 | 0.0022 | 0.0000 |
| 9.898 | 0.0037 | 0.0064 | 0.0055 | 0.0043 | 0.0000 |
| 9.947 | 0.0000 | 0.0046 | 0.0000 | 0.0000 | 0.0000 |
| 9.997 | 0.0055 | 0.0018 | 0.0000 | 0.0000 | 0.0000 |
| 10.047 | 0.0000 | 0.0009 | 0.0000 | 0.0022 | 0.0037 |
| 10.097 | 0.0018 | 0.0027 | 0.0027 | 0.0065 | 0.0000 |
| 10.148 | 0.0000 | 0.0027 | 0.0000 | 0.0000 | 0.0000 |
| 10.198 | 0.0055 | 0.0018 | 0.0000 | 0.0000 | 0.0000 |
| 10.249 | 0.0000 | 0.0018 | 0.0027 | 0.0043 | 0.0000 |
| 10.301 | 0.0018 | 0.0009 | 0.0027 | 0.0022 | 0.0000 |
| 10.352 | 0.0000 | 0.0018 | 0.0027 | 0.0000 | 0.0000 |
| 10.404 | 0.0018 | 0.0027 | 0.0000 | 0.0000 | 0.0000 |
| 10.456 | 0.0000 | 0.0009 | 0.0000 | 0.0000 | 0.0000 |
| 10.508 | 0.0018 | 0.0027 | 0.0000 | 0.0000 | 0.0000 |
| 10.561 | 0.0000 | 0.0046 | 0.0027 | 0.0000 | 0.0000 |
| 10.613 | 0.0000 | 0.0018 | 0.0000 | 0.0000 | 0.0000 |
| 10.666 | 0.0018 | 0.0000 | 0.0000 | 0.0000 | 0.0000 |
| 10.720 | 0.0000 | 0.0009 | 0.0000 | 0.0000 | 0.0000 |
| 10.773 | 0.0018 | 0.0092 | 0.0082 | 0.0000 | 0.0000 |

Figure 4I

| | | | | | |
|---|---|---|---|---|---|
| 10.827 | 0.0037 | 0.0027 | 0.0000 | 0.0087 | 0.0000 |
| 10.881 | 0.0018 | 0.0055 | 0.0055 | 0.0000 | 0.0000 |
| 10.936 | 0.0000 | 0.0009 | 0.0027 | 0.0022 | 0.0000 |
| 10.991 | 0.0037 | 0.0027 | 0.0027 | 0.0000 | 0.0000 |
| 11.045 | 0.0000 | 0.0018 | 0.0027 | 0.0022 | 0.0000 |
| 11.101 | 0.0000 | 0.0046 | 0.0027 | 0.0065 | 0.0018 |
| 11.156 | 0.0000 | 0.0009 | 0.0000 | 0.0065 | 0.0000 |
| 11.212 | 0.0018 | 0.0037 | 0.0000 | 0.0043 | 0.0000 |
| 11.268 | 0.0018 | 0.0046 | 0.0027 | 0.0022 | 0.0018 |
| 11.324 | 0.0000 | 0.0046 | 0.0027 | 0.0043 | 0.0037 |
| 11.381 | 0.0018 | 0.0046 | 0.0000 | 0.0000 | 0.0018 |
| 11.438 | 0.0018 | 0.0018 | 0.0000 | 0.0000 | 0.0037 |
| 11.495 | 0.0018 | 0.0027 | 0.0027 | 0.0022 | 0.0018 |
| 11.553 | 0.0037 | 0.0037 | 0.0027 | 0.0000 | 0.0018 |
| 11.610 | 0.0055 | 0.0082 | 0.0055 | 0.0000 | 0.0000 |
| 11.668 | 0.0037 | 0.0027 | 0.0027 | 0.0000 | 0.0018 |
| 11.727 | 0.0055 | 0.0064 | 0.0000 | 0.0000 | 0.0000 |
| 11.785 | 0.0000 | 0.0064 | 0.0000 | 0.0022 | 0.0018 |
| 11.844 | 0.0000 | 0.0037 | 0.0027 | 0.0000 | 0.0000 |
| 11.904 | 0.0000 | 0.0073 | 0.0027 | 0.0000 | 0.0000 |
| 11.963 | 0.0000 | 0.0037 | 0.0027 | 0.0000 | 0.0000 |
| 12.023 | 0.0000 | 0.0009 | 0.0000 | 0.0000 | 0.0000 |
| 12.083 | 0.0037 | 0.0018 | 0.0000 | 0.0022 | 0.0000 |
| 12.143 | 0.0000 | 0.0027 | 0.0000 | 0.0000 | 0.0000 |
| 12.204 | 0.0018 | 0.0000 | 0.0000 | 0.0000 | 0.0000 |
| 12.265 | 0.0018 | 0.0055 | 0.0000 | 0.0022 | 0.0000 |
| 12.326 | 0.0037 | 0.0027 | 0.0027 | 0.0000 | 0.0000 |
| 12.388 | 0.0000 | 0.0018 | 0.0000 | 0.0022 | 0.0000 |
| 12.450 | 0.0018 | 0.0018 | 0.0000 | 0.0000 | 0.0000 |
| 12.512 | 0.0055 | 0.0018 | 0.0000 | 0.0022 | 0.0000 |
| 12.575 | 0.0055 | 0.0018 | 0.0000 | 0.0022 | 0.0000 |
| 12.638 | 0.0000 | 0.0009 | 0.0000 | 0.0000 | 0.0000 |
| 12.701 | 0.0055 | 0.0018 | 0.0000 | 0.0000 | 0.0000 |
| 12.764 | 0.0018 | 0.0037 | 0.0000 | 0.0022 | 0.0000 |
| 12.828 | 0.0000 | 0.0027 | 0.0000 | 0.0000 | 0.0000 |
| 12.892 | 0.0037 | 0.0000 | 0.0000 | 0.0000 | 0.0000 |
| 12.957 | 0.0055 | 0.0009 | 0.0027 | 0.0000 | 0.0000 |
| 13.022 | 0.0018 | 0.0000 | 0.0000 | 0.0022 | 0.0000 |
| 13.087 | 0.0018 | 0.0009 | 0.0027 | 0.0000 | 0.0000 |
| 13.152 | 0.0037 | 0.0000 | 0.0000 | 0.0022 | 0.0000 |
| 13.218 | 0.0018 | 0.0000 | 0.0000 | 0.0022 | 0.0000 |
| 13.284 | 0.0055 | 0.0000 | 0.0000 | 0.0000 | 0.0000 |
| 13.350 | 0.0000 | 0.0000 | 0.0000 | 0.0022 | 0.0000 |
| 13.417 | 0.0018 | 0.0000 | 0.0000 | 0.0000 | 0.0000 |
| 13.484 | 0.0018 | 0.0000 | 0.0000 | 0.0000 | 0.0000 |
| 13.552 | 0.0000 | 0.0009 | 0.0000 | 0.0000 | 0.0000 |
| 13.619 | 0.0018 | 0.0009 | 0.0000 | 0.0000 | 0.0000 |
| 13.688 | 0.0037 | 0.0000 | 0.0000 | 0.0000 | 0.0000 |
| 13.756 | 0.0037 | 0.0000 | 0.0000 | 0.0000 | 0.0000 |
| 13.825 | 0.0018 | 0.0000 | 0.0000 | 0.0000 | 0.0000 |
| 13.894 | 0.0018 | 0.0000 | 0.0000 | 0.0000 | 0.0000 |
| 13.963 | 0.0018 | 0.0009 | 0.0000 | 0.0000 | 0.0000 |
| 14.033 | 0.0037 | 0.0018 | 0.0000 | 0.0000 | 0.0000 |
| 14.103 | 0.0018 | 0.0027 | 0.0000 | 0.0000 | 0.0000 |

Figure 4J

| | | | | | |
|---|---|---|---|---|---|
| 14.174 | 0.0018 | 0.0037 | 0.0000 | 0.0000 | 0.0000 |
| 14.245 | 0.0018 | 0.0018 | 0.0000 | 0.0000 | 0.0000 |
| 14.316 | 0.0000 | 0.0018 | 0.0000 | 0.0000 | 0.0000 |
| 14.387 | 0.0000 | 0.0027 | 0.0000 | 0.0000 | 0.0000 |
| 14.459 | 0.0018 | 0.0000 | 0.0000 | 0.0000 | 0.0000 |
| 14.532 | 0.0000 | 0.0018 | 0.0000 | 0.0000 | 0.0000 |
| 14.604 | 0.0000 | 0.0000 | 0.0000 | 0.0000 | 0.0000 |
| 14.677 | 0.0018 | 0.0000 | 0.0000 | 0.0000 | 0.0000 |
| 14.751 | 0.0018 | 0.0009 | 0.0000 | 0.0000 | 0.0000 |
| 14.825 | 0.0037 | 0.0000 | 0.0000 | 0.0000 | 0.0000 |
| 14.899 | 0.0000 | 0.0009 | 0.0000 | 0.0000 | 0.0000 |
| 14.973 | 0.0018 | 0.0009 | 0.0000 | 0.0000 | 0.0000 |
| 15.048 | 0.0000 | 0.0000 | 0.0000 | 0.0000 | 0.0018 |
| 15.123 | 0.0000 | 0.0000 | 0.0000 | 0.0000 | 0.0000 |
| 15.199 | 0.0018 | 0.0000 | 0.0000 | 0.0000 | 0.0000 |
| 15.275 | 0.0037 | 0.0000 | 0.0000 | 0.0000 | 0.0000 |
| 15.351 | 0.0000 | 0.0000 | 0.0000 | 0.0000 | 0.0000 |
| 15.428 | 0.0000 | 0.0000 | 0.0000 | 0.0000 | 0.0000 |
| 15.505 | 0.0018 | 0.0000 | 0.0000 | 0.0000 | 0.0000 |
| 15.583 | 0.0000 | 0.0000 | 0.0000 | 0.0000 | 0.0000 |
| 15.661 | 0.0000 | 0.0000 | 0.0000 | 0.0000 | 0.0000 |
| 15.739 | 0.0000 | 0.0000 | 0.0000 | 0.0000 | 0.0000 |
| 15.818 | 0.0000 | 0.0000 | 0.0000 | 0.0000 | 0.0000 |
| 15.897 | 0.0018 | 0.0000 | 0.0000 | 0.0000 | 0.0000 |
| 15.976 | 0.0000 | 0.0000 | 0.0000 | 0.0000 | 0.0000 |
| 16.056 | 0.0000 | 0.0000 | 0.0000 | 0.0000 | 0.0000 |
| 16.136 | 0.0000 | 0.0000 | 0.0000 | 0.0000 | 0.0000 |
| 16.217 | 0.0018 | 0.0000 | 0.0000 | 0.0000 | 0.0000 |
| 16.298 | 0.0000 | 0.0000 | 0.0000 | 0.0000 | 0.0000 |
| 16.380 | 0.0018 | 0.0000 | 0.0000 | 0.0022 | 0.0000 |
| 16.461 | 0.0000 | 0.0000 | 0.0000 | 0.0000 | 0.0000 |
| 16.544 | 0.0000 | 0.0000 | 0.0000 | 0.0000 | 0.0000 |
| 16.627 | 0.0000 | 0.0000 | 0.0000 | 0.0000 | 0.0000 |
| 16.710 | 0.0000 | 0.0000 | 0.0000 | 0.0000 | 0.0000 |
| 16.793 | 0.0000 | 0.0000 | 0.0000 | 0.0000 | 0.0000 |
| 16.877 | 0.0000 | 0.0000 | 0.0000 | 0.0000 | 0.0000 |
| 16.962 | 0.0000 | 0.0000 | 0.0000 | 0.0000 | 0.0000 |
| 17.046 | 0.0000 | 0.0000 | 0.0000 | 0.0000 | 0.0000 |
| 17.132 | 0.0000 | 0.0000 | 0.0000 | 0.0000 | 0.0000 |
| 17.217 | 0.0000 | 0.0000 | 0.0000 | 0.0000 | 0.0000 |
| 17.303 | 0.0000 | 0.0000 | 0.0000 | 0.0000 | 0.0000 |
| 17.390 | 0.0000 | 0.0000 | 0.0000 | 0.0000 | 0.0000 |
| 17.477 | 0.0000 | 0.0000 | 0.0000 | 0.0000 | 0.0000 |
| 17.564 | 0.0000 | 0.0000 | 0.0000 | 0.0000 | 0.0000 |
| 17.652 | 0.0000 | 0.0000 | 0.0000 | 0.0000 | 0.0000 |
| 17.740 | 0.0000 | 0.0000 | 0.0000 | 0.0000 | 0.0000 |
| 17.829 | 0.0000 | 0.0000 | 0.0000 | 0.0000 | 0.0000 |
| 17.918 | 0.0000 | 0.0000 | 0.0000 | 0.0000 | 0.0000 |
| 18.008 | 0.0000 | 0.0000 | 0.0000 | 0.0000 | 0.0000 |
| 18.098 | 0.0000 | 0.0000 | 0.0027 | 0.0000 | 0.0000 |
| 18.188 | 0.0000 | 0.0000 | 0.0000 | 0.0000 | 0.0000 |
| 18.279 | 0.0000 | 0.0000 | 0.0000 | 0.0000 | 0.0000 |
| 18.371 | 0.0000 | 0.0000 | 0.0000 | 0.0000 | 0.0000 |
| 18.462 | 0.0000 | 0.0000 | 0.0000 | 0.0000 | 0.0000 |

Figure 4K

| | | | | | |
|---|---|---|---|---|---|
| 18.555 | 0.0000 | 0.0000 | 0.0000 | 0.0000 | 0.0000 |
| 18.647 | 0.0000 | 0.0000 | 0.0000 | 0.0000 | 0.0000 |
| 18.741 | 0.0000 | 0.0000 | 0.0000 | 0.0000 | 0.0000 |
| 18.834 | 0.0000 | 0.0000 | 0.0000 | 0.0000 | 0.0000 |
| 18.929 | 0.0000 | 0.0000 | 0.0000 | 0.0000 | 0.0000 |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

CCCCCGTGT CGCTGTT 17

MOLECULAR GENETIC IDENTIFICATION USING PROBES THAT RECOGNIZE POLYMORPHIC LOCI

CROSS-REFERENCE TO RELATED APPLICATIONS

This is a continuation of application Ser. No. 08/050,746, filed Apr. 21, 1993, now abandoned, which is a continuation of application Ser. No. 07/650,511, filed Feb. 5, 1991, now abandoned.

FIELD OF THE INVENTION

The present invention relates to compositions and methods for identifying nucleic acid polymorphism. Specific applications of this invention include paternity testing, forensics, disease diagnosis, cell line identification and determination of chimerism/mosaicism as in distinguishing zygosity or following transplantation.

BACKGROUND OF THE INVENTION

Population variation can occur at the level of the organism, cell or a cellular component. Variability relating to a nucleic acid or protein is referred to as polymorphism. Traditionally, polymorphism focused on cell membrane proteins, serum-borne proteins and intracellular proteins. Applications included blood group testing, for example ABO or HLA, and isozyme analysis (Lewontin & Hubby, [1966] *Genetics* 54:595). These methods relied on amino acid changes that altered the molecular charge of the protein or an antigenic determinant. A limitation of the utility of protein polymorphism is that available methods may fail to detect an amino acid substitution if it occurs at an unexposed site.

Nucleic acid polymorphism can occur in both coding and noncoding segments. The characterization of polymorphism in coding sequences has been enhanced by the availability of HLA cDNA clones. Polymerase Chain Reaction (PCR) amplification coupled with allele specific probes has been used to analyze genetic polymorphism at several HLA loci. Potential problems with this methodology include PCR contamination and ambiguous typing results when the sequence detected by a given probe could be assigned to either of two alleles.

Traditional methods of nucleic acid hybridization have also been successfully applied to the study of genetic identification. One of the most powerful techniques is the procedure described by E. M. Southern (Southern, E. M. (1975) *J. Mol. Biol.* 98:503–517). This method involves the fractionation of the complex genetic material to be analyzed prior to hybridization. Such a genetic analysis can reveal not only the presence or absence of complementary target nucleic acid sequences, but also the size of the restriction fragment(s) containing the target sequence. Genetic variations within a species may be reflected by variations among individuals in the size of the restriction fragments containing a particular target sequence. Conversely, genetic relatedness of a group of individuals may be reflected by a deviation from random variations that exist among unrelated individuals. This aspect of genetic analysis has been called Restriction Fragment Length Polymorphism (RFLP).

A typical RFLP analysis involves digesting target genomic DNA with a restriction endonuclease, separating the digested DNA by gel electrophoresis, transferring the fractionated DNA to a denatured state to a binding surface, hybridizing the transferred DNA with a suitable probe, detecting the signals generated by the probe molecules which have become hybridized to the target DNA. The pattern of the signals generated would provide information about the target DNA. The pattern of signals can also be stored for later use, for instance, to determine or confirm an individual's identification (i.e., the pattern would be the individual's genetic fingerprint).

More commonly, two or more target DNAs are processed for RFLP analysis. Depending on the sources of the target DNA, the information generated by comparison of the patterns can be used immediately as in the case of genetic identity (e.g., identification of a suspect of a crime), or in the case where a high degree of genetic relatedness is present (e.g., paternity testing, sib analysis and the like). In other cases, the information derived from pattern comparison may form a part of a larger information-gathering effort. Pedigree analysis of distant relatives and correlation of a gene or genotype with a trait or medical condition are two examples.

The genetic information which can be adduced using "single-copy" DNA probes depends on the number of probes used, the number of genetic loci each probe is capable of detecting, as well as the heterozygosities and allele frequency of the relevant genetic loci. To date, "single-copy" DNA sequences are known to detect only a single locus per sequence. Moreover, heterozygosity of DNA in higher organisms is low. In man, it is about 0.001 per base pair. Finally, most polymorphic states detected are only dimorphic (i.e. there are only two representational states: absence or presence of a relevant restriction site on the restriction fragment in question). As is often the case, critical individuals in a genetic analysis are homozygous, and the genetic analysis may be uninformative.

Genetic analysis in higher organisms has been simplified considerably by the availability of probes for hypervariable regions of genomic DNA. These hypervariable regions show multi-allelic variation and high heterozygosities. These regions also appear to be widely interspersed within the genome. In each case, the hypervariable region comprises a variable number of tandem repeats of a short sequence (thus, Variable Tandem Repeats or VTR), and polymorphism results from allelic differences in the number of repeats at a given locus. This type of polymorphism, a subclass of RFLP has been called VTR Polymorphism. It is believed that the variation in repeat number arises by mitotic or meiotic unequal exchanges or by DNA "slippage" during replication. Therefore, if genomic DNA is digested with a restriction endonuclease which does not cut within the repeat unit, and if a genetic locus encompasses a variable tandem repeat or VTR, allelic markers would exist for that locus. It should be noted that the so-called repeat unit is a hypothetical consensus sequence, and any VTR sequence in the genome is actually a string of short "core" sequences, each of which is very highly homologous, but usually not identical to the consensus sequence. In deed, a "core" sequence may differ in length from the consensus sequence. The consensus sequence is derived from examining and "averaging" a large number of "core" sequences and is typically at least 70%, but often more than 70% homologous to the consensus sequence.

The utility of clones that detect highly polymorphic loci is evidenced by the White et al. patent (U.S. Pat. No. 4,963,663) and the references cited therein.

However the RFLP analysis is to be used, the pattern of signals is controlled in large part by the probe or probes used in the analysis. A polynucleotide probe may be useful for any of a number of features.

First, a probe may be able to detect polymorphism at a locus that other probes cannot detect. The locus may be particularly useful for genetic analysis in the general population because it has many evenly distributed alleles. Alternatively, the locus may be particularly useful for genetic analysis in a highly restricted segment of the population because it has a rare allele.

Second, a probe may be able to detect many loci simultaneously and unambiguously when a particular restriction endonuclease is used to digest the target DNA. In this connection, it is useful to note that certain restriction endonucleases may be preferred because of the history of the target DNA samples, e.g. forensic samples which have been exposed to the elements for an extended period of time.

Third, probes are often used in combination simultaneously because their resolving power may be compounded. Compounding is obtained when the signals produced by the several probes do not overlap and permit unambiguous assignment of each (or substantially each) signal to an allele of a locus. See, e.g., Baird et al. (1987) "The Application Of DNA-Print For The Estimation Of Paternity," in *Advances in Forensic Haemogenetics* 2:354–358, Springer-Verlag, N.Y.

A polymorphic DNA locus, recognized by a probe, can be defined by the unique identification number that is assigned by the Human Gene Mapping Library or Genome Data Base. The probe described in this invention recognizes the DNA locus of chromosome 4 which has been assigned the number D4S163. In other words, the polynucleotide sequence utilized in the probe reacts or has a DNA sequence complementary to the genomic DNA at the D4S163 locus of human chromosome 4.

How RFLP phenotypes can be practically applied for paternity and forensic determinations have been discussed in Baird et al., supra; Baird et al. (1987) (II) "The Application Of DNA-PRINT For Identification From Forensic Biological Materials," in *Advances in Forensic Haemogenetics* 2:396–402, Springer-Verlag, N.Y.; and Baird et al. (1986) *Am. J. Hum. Genet.* 39:489–501.

An alternative approach for the genetic analysis, of this type of Variable Tandem Repeat containing regions, may utilize a method that replicates the DNA in the laboratory, in a cell-free system. This replication process can be repeated multiple times so as to produce the specific DNA in amounts sufficient for analysis. By using as primers for replication, polynucleotide sequences complementary to the opposite strands of the DNA sequence flanking the VTR, the size of the product will be determined by the total length of the VTR region. Cetus Corporation has been assigned patents that cover certain forms of this procedure (U.S. Pat. Nos. 4,683,202 and 4,683,195). Examples on the use of this process for replicating nucleic acids from regions of DNA containing VTR can be found in Boerwinkle et al. (1989) *Proc. Nat. Acad. Sci. USA* 86:212; Horn et al. (1989) *Nucleic Acid Res.* 17:2140; Wu et al. (1990) *Nucleic Acid Res.* 18:3102; and Kasai et al. (1990) *J. Foren. Sci.* 35:1196.

BRIEF SUMMARY OF THE INVENTION

The subject invention concerns the following:

(1) polynucleotide sequences, defined by a sequence similar to that found at the human locus D4S163, useful for detecting polymorphism in a species of organism of interest, or a subpopulation thereof;

(2) a polynucleotide sequence useful for detecting polymorphism at one or more genetic loci, and characterized by its ability to form hybrids with restriction fragments of DNA, for the locus D4S163 in chromosome 4, of about 8.2 and about 7.07 kilobases, produced by PstI digestion of genomic DNA from K562 cells; of about 4.4 and about 4 kilobases, produced by HaeIII digestion of genomic DNA from K562 cells.

(3) a polynucleotide sequence useful for detecting polymorphism at the single genetic locus, D4S163, and capable of forming hybrids with genomic DNA fragments produced by complete digestion of Caucasoid, American Black, or Oriental genomic DNA with the restriction endonuclease PstI of approximate allelic lengths and allelic frequencies as given in FIGS. 4A–4K;

(4) the use of the above-described polynucleotide sequence as a probe for polymorphism;

(5) a method of genetic analysis comprising: (a) digesting a DNA sample with a restriction endonuclease; (b) separating the DNA restriction fragments according to size by electrophoresis; (c) transferring the separated DNA to a binding surface; (d) hybridizing the transferred DNA with a polynucleotide probe labeled with a signal-generating moiety; and (e) detecting the signal generated; whereby the pattern of signals generated provides information about the composition of the DNA sample; and (6) recombinant vectors and cells useful for producing polynucleotides of the invention.

BRIEF DESCRIPTION OF THE DRAWINGS

FIGS. 4A–4K show allele frequencies for different racial groups.

BRIEF DESCRIPTION OF THE SEQUENCES

Figure 1:
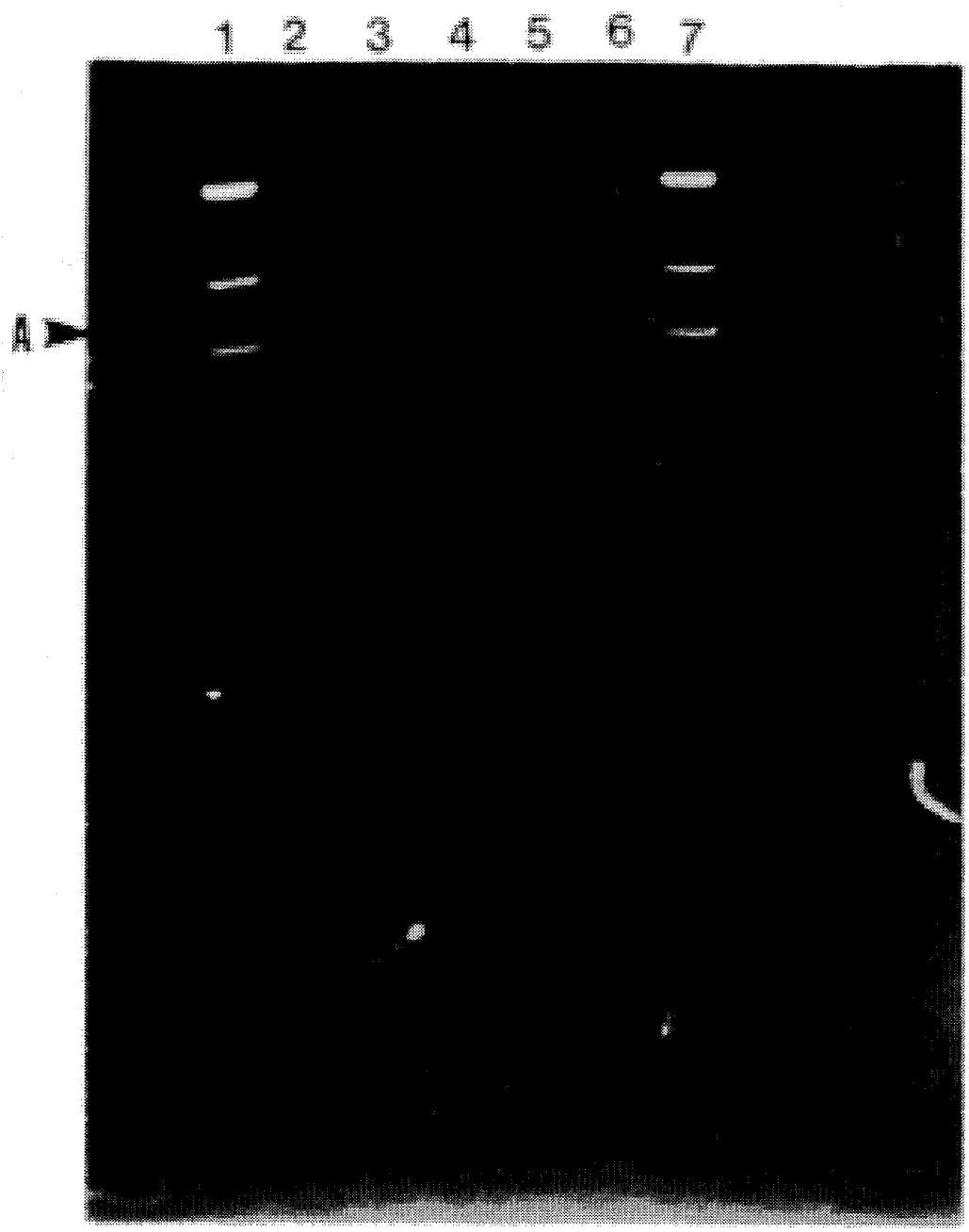
FIG. 1 shows the electrophoretic pattern of restriction fragments of DNAs from the recombinant lambda phage Lila 5 which was digested with EcoRI. Lanes 1 and 7 correspond to HindIII digested lambda DNA marker. The Lila 5 EcoRI digest is shown in lanes 2 through 6. A human genomic insert is identified as Band A.

SEQ ID No. 1 the consensus sequence of the screening probe used according to the subject invention.

DETAILED DESCRIPTION OF THE INVENTION

One embodiment of the instant invention is a method to obtain polynucleotide sequences useful for detecting polymorphism in a species, or a subpopulation thereof. A library of genomic DNA digested with one or more restriction endonucleases and cloned in a suitable recombinant vector is screened with a polynucleotide probe which comprises a string of "core" sequences (hereinafter "screening probe"). This string of "core" sequences can, but need not be, a monomer, an oligomer or a polymer or a mixture of oligomers and polymers of a consensus sequence or "core" sequence of a VTR. Preferably, the screening probe is a mixture of oligomers of a consensus sequence, because a short consensus sequence can be easily synthesized chemically in large amounts and ligated to form a mixture of oligomers. In a preferred embodiment, the consensus sequence is 5'-CCCCCCGTGTCGCTGTT-3' (SEQ ID No. 1). For the purpose of generating a genomic library, it is preferred that the restriction endonuclease digestion of genomic DNA be incomplete. One reason is that many genomic VTR sequences may otherwise evade detection. This would be so if the relevant restriction endonuclease cuts within the VTR sequences and the bulk of the VTR sequences will be in relatively small pieces. The smaller the pieces, the greater the number of recombinant molecules which must be studied so that the human genome will be covered. For the same reason, it is preferred that a recombinant vector which can accommodate a large DNA insert be used. Finally, where the recombinant vector has a restricted cloning range, incomplete digestion of the genomic DNA would also tend to avoid under-representation in the library of completely digested products which are smaller than the preferred cloning sizes.

The recombinants which react positively with the screening probe in a hybridization test (hereinafter "positive recombinants") are selected for further examination. In a preferred embodiment, the recombinants are bacteriophages.

The standard method of "phage lifts" can be used to identify the recombinants containing DNA inserts which hybridize to the probe. See Sambrook et al., *Molecular Cloning: A Laboratory Manual*, Cold Spring Harbor Laboratories, Cold Spring Harbor, N.Y., (1989).

Once the positive recombinants have been identified, they can be subjected to tests which prove or disprove their utility. They are used as probes in hybridization tests against genomic sequences of a species of organism of interest, or a relevant subpopulation thereof. While the present invention broadly encompasses eukaryotic organisms, one of the more commercially significant uses is the probing of mammalian genomes, particularly, the human genome. It is very highly preferred that the probe sequences of the present invention be derived from the same species of organisms as the genetic materials which are to be tested in a hybridization test. Thus, for applications of human genetic analysis, the starting library preferably should be a human genomic library. To avoid verbosity, the embodiments of this invention are described as if they apply to humans specifically. The present invention is not so limited, and is to be construed to be applicable generally to mammals and other eukaryotes.

The most useful positive recombinants are those which can detect high levels of polymorphism in humans, at a single locus, and under high stringency conditions. Genomic DNAs from related individuals are separately digested with a restriction endonuclease, the digests are subjected to size fractionation by, for example, electrophoresis, and the fractionated restriction fragments are prepared for hybridization by any standard method. Positive recombinants, or the human sequences or polynucleotide subsequences inserted therein (jointly and severally "test sequences") are used to probe the restriction digests. Preferably, a single test sequence is used at a time. However, several sequences can be grouped together in preliminary tests to determine whether the group as a whole contains any useful sequences.

Sequence homology requirements change when using longer nucleic acid fragments as probes for unique sequences because the length and relative content of G/C pairs of the fragment contribute to hybridization kinetics and, thus, fidelity of pairing (see, for example, Wetmur and Davidson [1968] *J. Mol. Biol.* 31:349). Hence, if one is performing an evolutional survey of a gene sequence, hybridization conditions would be modified to accommodate sequence divergence due to genetic drift. Nevertheless, the function of the sequences and the polypeptides encoded are conserved. On the other hand, if the desire is to identify sequences at a particular locus, hybridization conditions are modified so that a high degree of complementarity of the hybridizing components is required to maintain the duplex. VTR regions impose additional considerations in determining requisite sequence homology. Copy number variation contributes significantly to heterozygosity but often not all repeat units at a locus are identical. Thus, nucleic acid fragments that differ slightly in sequence may nevertheless hybridize to the same locus. Here, sequence homology may be defined in terms of those nucleic acid fragments that hybridize to a unique VTR locus for indeed it is the VTR locus and its detection that are paramount to the instant invention.

The hybridization "banding" pattern for each individual member is determined. In particular, the sizes of restriction fragments which hybridize to the test sequences are determined. The segregation scheme of each band within a family or, more commonly, a number of families will inform as to the nature of the genetic locus (loci) being detected. The nature of a genetic locus includes, but is not limited to, the following: (1) Mendelian or non-Mendelian segregation; and (2) phenotype and frequency of alleles (reflected by the size of genomic DNA restriction fragments produced by the restriction endonuclease, and the frequency of occurrence in a population). If the test sequence detects bands of a locus that represent different-sized fragments among different individuals, it is capable of detecting polymorphism at that polymorphic locus.

The determination of the nature of the locus (loci) detected by a test sequence from the segregation scheme is a straightforward application of classical genetics, and is well within the command of a person skilled in the art of molecular genetics. The size of families, and the number of families needed to provide sufficient information to work out the segregation scheme would vary with the number of genetic loci being detected by the test sequence, the number of alleles in these loci, and the frequency of each allele. An ordinarily skilled artisan would also know how to determine the number and size of families to be studied.

The instant invention provides test sequences which can detect polymorphism in a species of organism of interest, or a subpopulation thereof (hereinafter "useful test sequence").

In one embodiment of the instant invention, useful test sequences are cloned in recombinant vectors. In another embodiment, the recombinant vectors comprising the useful test sequences are harbored in a cell. Molecular cloning and transformation methods are well known in the art.

Because family segregation studies are both lengthy and expensive to resolve, it is sometimes preferable to defer the family studies until a test sequence has been better characterized. Thus, it may be preferable to modify the method described hereinabove. Specifically, genomic DNAs from random, unrelated individuals may be used instead of genomic DNAs from members of families. If the banding pattern appears to vary from individual to individual, the test sequence is presumptively treated as a useful polymorphic probe.

To produce an improved test sequence, the presumptively useful test sequence is analyzed, and less desirable sequences are removed. For example, a test sequence may comprise a subsequence which is polymorphic as well as a subsequence which is non-polymorphic in the relevant population. The presence of non-polymorphic bands yields no useful genetic information about a human individual and may interfere with genetic analysis. Such interference may occur, for example, when a non-polymorphic band obscures a partially or totally informational band detected by a second probe used in combination with the test sequence. Another example of potential genetic analysis interference is where the test sequence comprises a subsequence which is a highly repetitive sequence in the human genome such as the "Alu sequence." See Houck et al. (1989) *J. Mol. Biol.* 132:289–306. Presence of such highly repetitive sequences in a probe often causes a high, non-informational background signal in a hybridization blot. This background signal can be avoided by eliminating the highly repetitive sequence component from the test sequence. See, for example, Sealey et al. (1985) *Nucleic Acids Res.* 13:1905–1922.

Still another example is where the test sequence comprises a first subsequence which delivers only a small signal in a hybridization blot relative to the signal delivered by a second subsequence. Here, it may be more advantageous to eliminate the first test subsequence so that a more "cost-effective" probe may be produced which delivers a higher signal per nucleotide. A more specific example of this type is where the first subsequence is a "single-copy" sequence, and the second subsequence is a Variable Tandem Repeat sequence. The second sequence delivers more signal per nucleotide whenever more than a single copy occurs at a genetic locus.

Discrete polynucleotide subsequences can be obtained from a test sequence in a number of ways, and are well within the capability of an ordinarily skilled artisan. For example, one end of the test sequence may be incrementally removed by an exonuclease or S1 nuclease, while the other end is being protected.

Another example of obtaining discrete polynucleotide subsequences is by digestion with a restriction enzyme. Other methods of obtaining subsequences are within the realm of the present invention.

For the purpose of this invention, a "discrete polynucleotide sequence or subsequence" means a nucleic acid sequence of greater than 15 nucleotides, but preferably greater than 50 nucleotides; and a polynucleotide means a chain of about 15 nucleotides or more, and embraces the upper range of what is sometimes termed an oligonucleotide.

After the less desirable subsequences have been eliminated from a test sequence, the remaining portion of the test sequence is used in familial tests for the determination of the nature of the genetic locus (loci) which it is capable of detecting as described above.

Finally, nearby genomic sequences (including nearby VTR sequences) may be reached by chromosome walking.

As discussed in the Background section of this application, duplex formation and stability, depend on substantial .complementarity between the two strands of a hybrid, and a certain degree of mismatch can be tolerated.

Therefore, whenever a test sequence is obtained as described hereinabove and has been determined to be useful in probing target polynucleotides of interest, it is part of the present invention. This includes mutations (both single and multiple), deletions, insertion of the useful test sequence, and combinations thereof, wherein said mutations, insertions and deletions permit formation of stable hybrids with said target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) determining analytically the sequence of a test sequence of the present invention, synthesize chemically or otherwise an artificial sequence which is a mutation, insertion or deletion of the test sequence;

(2) using a test sequence of the present invention to obtain via hybridization a genomic test sequence or a mutation, insertion or deletion of the test sequence; and (3) mutating, inserting or deleting a test sequence in vitro or in vivo.

It is important to note that the mutational, insertional, and deletional variants generated from a given test sequence may be more or less efficient than the test sequences, in the sense that (a) more or fewer genetic loci may become detectable, (b) more or fewer alleles of a particular locus may become detectable, (c) more or less stable under stringent hybridization conditions, and (d) any combination of the above. Notwithstanding such differences in efficiency, these variants are within the scope of the present invention. In another embodiment of the present invention, the useful test sequences described hereinabove are used for genetic analysis (i.e., used as probes), including but not limited to analysis of genetic identity, relatedness, or alteration.

Thus, mutational, insertional, and deletional variants of the disclosed test sequences can be readily prepared by methods which are well known to those skilled in the art. These variants can be used in the same manner as the test sequences so long as the variants have substantial sequence homology with the test sequences. As used herein, substantial sequence homology refers to homology which is sufficient to enable the variant to function in the same capacity as the test sequence. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

In addition to the test sequences described herein the subject invention further pertains to the use of these test sequences for genetic analysis. In one preferred embodiment, the method of genetic analysis comprises:

(a) digesting a DNA sample with a restriction endonuclease;

(b) separating the DNA restriction fragments according to size by electrophoresis;

(c) transferring the separated DNA in a state suitable for hybridization to a binding surface;

(d) hybridizing the transferred DNA with a useful test sequence labeled with a signal-generating moiety, and (e) detecting the signals generated; whereby the pattern of signals generated provides information about the composition of the DNA sample.

In order to accomplish the identification of individuals or tissue samples within the scope of the present invention, one or more loci of interest are analyzed using standard filter hybridization technologies. As was discussed previously, a VTR locus having multiple alleles which occur at different frequencies in the population is preferred.

In order to initiate the testing procedure, a tissue sample is obtained. It will be appreciated that the sample may comprise any type of tissue. For most applications, it is likely that blood would be the tissue of choice. This would be true in the case of paternity testing and the like. However, other tissues, including skin, semen, hair, and other body fluids or tissues may be acceptable for specific purposes. Using the methods of the present invention, no more than approximately 10 µl of blood is required in order to perform the testing procedure. DNA can be obtained from any nucleated cell that is live, dead, or preserved.

The testing procedure generally requires that the cells in the tissue sample be lysed and that the DNA obtained from the lysed cells be isolated and cleaved with a restriction enzyme. It should be appreciated that because the variability at a VTR locus arises from copy number differences of tandem repeats, any restriction endonuclease with sites flanking the repeats will reveal the polymorphism. The enzymes noted in the specification are representative and are non-limiting examples of enzymes which can be used for a VTR clone. In a preferred embodiment, restriction enzymes with sites very close to the cluster of repeats are desired. The result is smaller restriction fragments which are easier to discriminate on agarose gels. The DNA can then be applied to gel and electrophoresed using widely known and generally accepted procedures. The DNA is then denatured such that it exists in the single strand form.

At this point, the DNA can be transferred to a membrane according to the technique of Southern (Southern, E. M. [1975] *J. Mol. Biol.* 98:503) which is widely practiced and accepted in the art.

The DNA thus isolated and denatured is hybridized with one or more labeled VTR sequences of the type described above. Following wash, the location of the labeled nucleic acid fragment is determined using techniques such as an autoradiogram of the membrane filter. It will be appreciated that while radiolabeling of the probe is emphasized herein, labeling by other methods is acceptable. Labeling with fluorescent dyes or with biotinylated nucleotides, for example, has worked as well as radiolabeled probes. It is only necessary that the location of the hybridized nucleic acid fragment be determinable.

The specific location of the hybridized duplex provides information concerning the particular characteristics of the DNA. By employing multiple probes for multiple VTR loci, it is possible to provide a very accurate genetic identification of an individual from which the tissue samples were obtained. Thus, it is possible to compare the results with that individual or with possible parents or offspring of the individual to identify, not only the individual, but the paternity of the individual.

The present invention can determine paternity with virtual certainty. Multiple probes of multiple VTR loci can be employed. Each locus chosen will have multiple alleles occurring at various frequencies in the population. Thus, by employing a plurality of probes, the probability of two individuals producing the same VTR pattern becomes essentially zero.

The same technique is employed when it is desired to link a tissue sample with a specific individual. For example, if a sample of tissue or body fluid is found at a crime scene, using the present invention, that sample can be tied precisely to a particular individual.

Similarly, in the case of bone marrow transplants, it is desirable to determine whether an individual's cancerous cells have begun to regenerate. Thus, cells are removed and analyzed according to the present invention. If the results from the bone marrow match those from the patient, it is possible that cancerous cells are reappearing. Similarly, if the results from the bone marrow do not match the recipient, it is clear that only transplanted cells exist.

Numerous other applications are also possible, some of which have been discussed above. These may include, for example, determining monozygosity versus dizygosity in twins, identifying potential organ donors, forensic applications, identification of diseased genes, and mapping of the genome.

Methods for the use of probes such as those described herein are well known to those skilled in this art. There are a variety of techniques which can be used to enhance the effectiveness of these probes or to maximize their utility for a particular application. For example, PCR amplification of the sample DNA, increasing label signal by concentrating more label at the target site or using multiple-labeled probes (or combining these label enhancer methods), using a secondary probe to the hybridized primary probe, and amplification of hybridized probes, particularly recombinant RNAs that serve as templates for Qβ are techniques that provide enhanced effectiveness of the probes and are well known to those skilled in the art. These procedures are described, for example, in U.S. Pat. No. 4,963,663 and the references cited therein.

Following are examples which illustrate procedures, including the best mode, for practicing the invention. These examples should not be construed as limiting. All percentages are by weight and all solvent mixture proportions are by volume unless otherwise noted.

Example 1-Detection of Genomic Sequences which Hybridize with Oligomers of a Consensus Sequence of a VTR Human genomic DNA incompletely digested with the restriction endonuclease EcoRI was cloned into the bacteriophage lambda Charon 30 [*Gene* 12:301–309 (1980)]. Approximately 5000 phage plaques were screened according to the method of Sambrook et al., supra, at page 1.90. Oligomers of 5'-CCCCCCGTGTCGCTGTT -3' (SEQ ID No. 1), the 17-base consensus sequence of VTR at the 3' end of the human alpha globin complex, with an average length of 200–300 bases, were used to screen the phage "lifts."

Example 2-Analysis of Human Sequences in the Recombinant Phage Lila 5

A number of recombinant phages whose DNA hybridized with oligo-5' -CCCCCCGTGTCGCTGTT-3' (SEQ ID No. 1) were analyzed. The results obtained with the phage designated Lila 5 are presented below. DNA from Phage Lila 5 was extracted and digested with the restriction endonuclease EcoRI (FIG. 1). The digests were subjected to electrophoresis in an agarose gel. Lane 1 of the gel contained bacteriophages lambda HindIII fragments as molecular weight marker. Band A in FIG. 1 is the human genomic sequence insert of approximately 7 Kb in size.

Example 3-Human Genomic Sequence Inserts from Phage Lila 5 as Polymorphic Probes To characterize the human genomic inserts in Phage Lila 5 DNA corresponding to the human genomic sequence identified in Example 2 was isolated. It was used, in the Southern format, to probe human genomic DNAs from unrelated individuals. Target human sequences were restricted with PstI.

Five micrograms of PstI digested DNA from each individual was electrophoresed and blotted onto a nylon membrane. The probe, pAC400 insert, corresponded to [alpha-P32]-labeled DNA of the human genomic sequence of Example 2. Radioactive labeling was achieved by random 6-mer primed enzymatic synthesis, using radioactive precursors as substrates. However, other methods of labeling would work as well. Total unlabeled human genomic DNA was added to the 7 Kb probe as a precautionary measure. It is known that the human genome contains widely dispersed highly repetitive sequences such as the Alu sequences. If the human insert in Phage Lila 5 contains these and/or similar highly repetitive sequences, such repetitive sequences could produce a heavy background signal over the entire area on the blot where human target DNA could be found. The introduction of total human genomic DNA would serve to suppress this background signal. Sealey et al., supra. All hybridizations were carried out at 65° C. in 5× SSPE, 1–2% SDS (sodium dodecylsulfate), 0.5–1 mg/ml heparin. The blots were washed in 0.1× SSC, 2.5 mM sodium phosphate, 1% SDS at 65° C., [1× SSPE=0.16M NaCl, 0.01M sodium phosphate, and 1 mM EDTA (ethylenediaminetetraacetic acid); 1×SSC=0.15M NaCl, 0.015M sodium citrate]. The blots were exposed at −70° C.

Analysis of the autoradiograms revealed a highly polymorphic pattern with an allele distribution of about 4 to about 16 Kb with the 7 Kb fragment probe. In addition, a DNA fragment of about 4 Kb was detected in all individuals examined, as well as rare polymorphic bands near 4 Kb and at about 3.4 Kb. Consequently, the 7 Kb fragment was isolated and further characterized.

Example 4-Cloning of the Human "Polymorphic Probe" Sequence from Phage Lila 5

Figure 2:
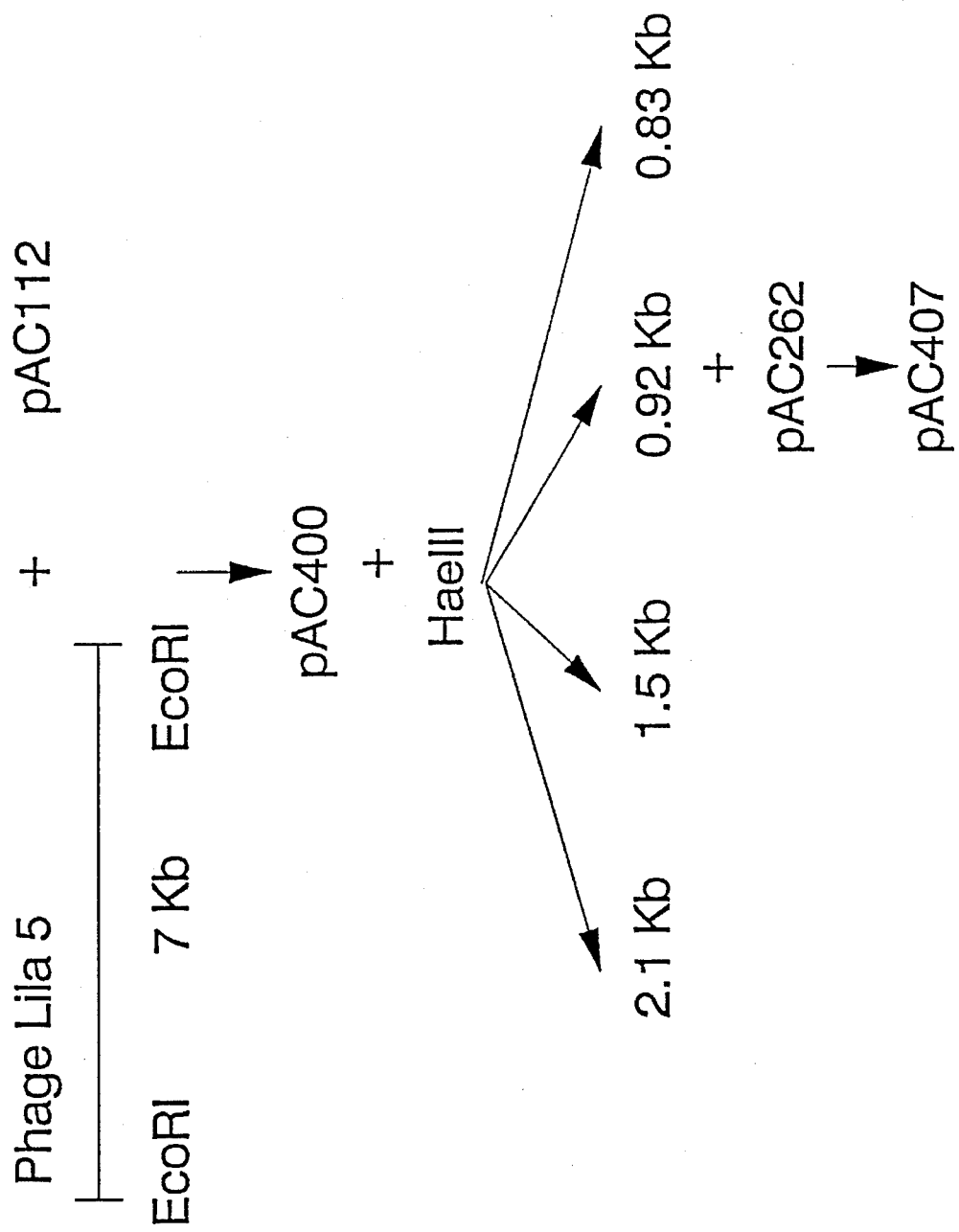
FIG. 2 is a schematic representation of the plasmid subclones of the phage designated Lila 5. The pAC400 probe contains the insert of approximately 7 Kb from the phage. The pAC407 probe was derived from the insert in pAC400.

The 7 Kb fragment described above was isolated and inserted into pAC112 (Bluescribe, Strategene Inc.) restricted with EcoRI. The resulting construct was identified as pAC400 (FIG. 2). The human sequence insert in pAC400 was further subcloned by isolating the 7 Kb insert and digesting it with HaeIII. The digest resulted in the generation of 4 DNA fragments of about 2.1, 1.5, 0.92 and 0.83 Kb in size. The HaeIII fragment corresponding to a size of about 0.92 Kb generated a polymorphic pattern on PstI blots. This 0.92 Kb fragment was isolated and ligated into pAC262 (Bluescript, Strategene Inc.) restricted with Sinai, resulting in pAC407. Interestingly, the insert from pAC407 produces a strong signal on PstI blots. A schematic representation of the subcloning of Lila 5 is shown in FIG. 2.

Example 5-pAC407 Detects a Single Locus which Segregates Independently in the Mendelian Fashion Genomic DNAs extracted from individuals belonging to families spanning three generations were digested with PstI or HaeIII, and probed with the pAC407 insert in the Southern format.

Each and every band which was present in any one of the eight children was also present in either the father or the mother. This result is consistent with stable chromosomal inheritance. Similarly, every band which was present in the parents was present in their respective parents (i.e., the grandparents).

In addition, the results were consistent with independent Mendelian segregation of alleles present on sister chromosomes. For example, in HaeIII digested DNA, bands appear to be two alleles to the same gene.

Example 6-Population Genetics and Allele Frequency

DNA from 950 genetically unrelated individuals were tested in this study. Each DNA sample was digested with PstI and probed with pAC407. The results were sorted according to the ethnic origin of the sample (i.e., American Blacks, Caucasoids, and Chinese Orientals). The frequency versus allele size distribution is presented in FIGS. 4A–4K. D4S163 is the assignment number designated by the Human Gene Mapping Library. In addition, about 500 individuals were digested with HaeIII and also hybridized with pAC407. These results are also presented in FIGS. 4A–4K.

Example 7-Characterization of pAC407

Genomic DNA from various human cell lines was extracted, digested with PstI, and hybridized with radioactively labeled pAC407. Samples # 8107, 8108 and 8095 were obtained form Centre d'Etude du Polymorphisme Humain in France. The erythroleukemia cell line K562 can be obtained from the American Type Culture Collection (ATCC) under ATCC catalog numbers CCL243.

The bands detected in the Southern blot are set forth in Table 1 below. For example, the pAC407 insert detected 2 polymorphic bands of about 8.2 and about 7.07 kilobase pairs when hybridized with PstI digested K562 cell DNA. The banding pattern obtained for each cell line is unique. Therefore, when used for probe purposes polynucleotide sequences can be characterized, or "fingerprinted" by the banding pattern with known target DNA.

TABLE 1

| Size of D4S163 DNA fragments detected with pAC407 | | | | |
| --- | --- | --- | --- | --- |
| | CELL LINE # | | | |
| Restriction Enzyme | 8108 | 8107 | 8095 | K562 |
| | DNA FRAGMENT SIZE (Kb) | | | |
| PstI | 8.9 | 10.6 | 8.19 | 8.2 |
| | 5.8 | 8.24 | 6.1 | 7.07 |
| HaeIII | 5.2 | 7.04 | 4.5 | 4.4 |
| | 2.1 | 4.5 | 2.3 | 4.0 |

Example 8-Paternity Testing

Figures 3A, 3B:
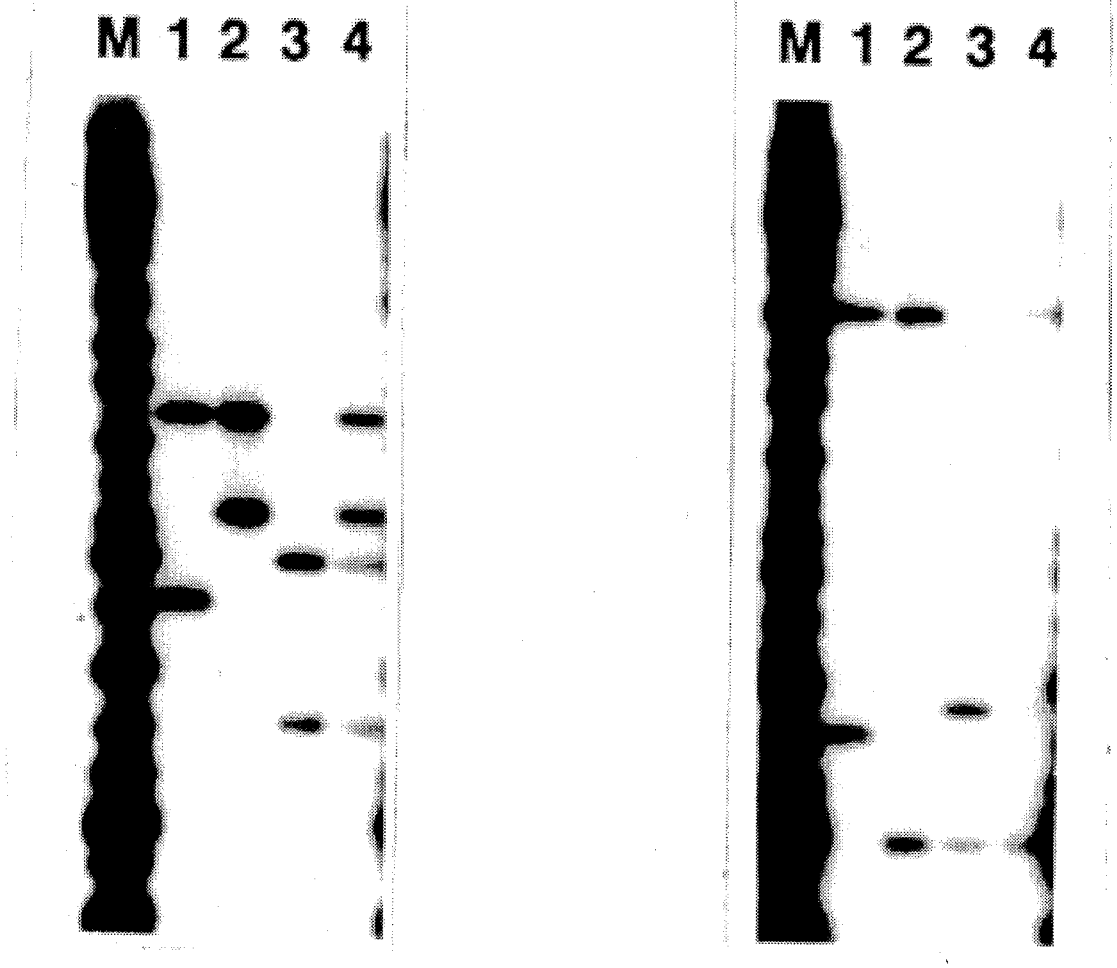
FIGS. 3A–3B shows the result of the hybridization blot for a paternity test using pAC407 as a probe. M: size markers; 1: DNA of mother; 2: child; 3: alleged father; 4: mixture of DNA from child and alleged father. (A) Example of paternal exclusion; (B) Example of paternal non-exclusion.

Genomic DNAs were extracted from a child, the mother of the child, and the alleged father. The DNAs were digested with PstI, electrophoresed, and transferred to a nylon membrane for hybridization. The DNA targets were probed with pAC407. FIGS. 3A–3B show the results of the hybridization blot. Lanes 1, 2, and 3 contained DNA from the mother, the child, and the alleged father of the child, respectively. Lane 4 contained a mixture of the child's DNA and the alleged father's DNA. The lane containing the mixture often helps to resolve ambiguity whenever a band detected in the child's lane is close in size to a band detected in the alleged father's lane. In such a case, the presence of a single band in the relevant size region in the "child plus alleged father" lane would tend to indicate a common allele; and a doublet band would indicate distinct alleles. FIG. 3B shows that one Band in the child was inherited from the mother, but the other was not inherited from the mother. Since the other band was also present in lane 3, the evidence supports the theory that the alleged father is indeed the biological father. FIG. 3A shows that one band in the child was inherited from the mother but the other did not come from the alleged father. This result would support the theory that the alleged father is not the biological father of this child.

Example 9-Forensic Testing

DNAs were extracted from a rape victim, semen stains found on the victim, and from a suspect of the crime. The DNAs were digested with PstI and subjected to the hybridization procedure. pAC407 was used as a probe. One sample contained Control DNA from the cell line K562. A second sample contained DNA from the victim. Two additional samples contained DNA from evidence found on the victim, and a final sample contained DNA from the suspect. Two bands found in the 7 to 12 Kb size range, in the various DNA samples, only matched between victim and suspect samples. Therefore, the results are consistent with the hypothesis that the semen stains derived from the suspect.

Example 10-Chromosomal Mapping

The clone pAC407 was mapped to human chromosome 4 by DNA hybridization analysis of human-mouse somatic cell hybrids. The presence or absence of fragments detected by the probe pAC407 was determined for 14 karyotyped hybrids (Table 2). These fragments were always seen when chromosome 4 was present in the hybrid cell line, but were not seen when chromosome 4 was absent. These data clearly assign the fragments detected by pAC407 to chromosome 4.

TABLE 2

Human Chromosomal composition of hybrid cell lines used for chromosome assignment.

| CELL LINE | D4S163 LILA5 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | MARKER CHROMOSOMES |
|---|---|---|---|---|---|---|---|---|---|---|---|---|---|---|---|---|---|---|---|---|---|---|---|---|---|---|
| HUMAN CTRL. | + | + | + | + | + | + | + | + | + | + | + | + | + | + | + | + | + | + | + | + | + | + | + | + | + | |
| B82 MS2 | + | + | + | + | + | − | − | + | + | − | − | + | + | + | + | + | + | − | + | + | − | + | + | + | + | |
| RAG ANLY 1 | − | + | − | + | + | − | + | + | + | + | − | − | * | + | * | * | − | − | − | − | − | + | − | * | − | Xqter-Xp22:15q13-15qter |
| RAG PI 7-2 | + | + | − | + | − | + | + | + | + | + | − | − | * | + | − | + | + | − | − | − | − | + | + | * | − | Xqter-Xp22:15q13-15qter |
| RAG PI 5-15 | + | + | + | + | + | + | + | + | + | − | + | + | + | − | + | − | + | − | + | + | + | + | + | * | − | Xqter-Xp22 |
| RAG 194-7 | + | + | + | * | + | + | − | − | + | − | + | − | * | − | + | − | − | − | + | − | − | + | + | * | − | Xq28-Xqter:3q21-3pter |
| RAG 194-5-5 | + | − | − | + | + | + | + | + | − | − | − | − | + | + | + | + | − | + | + | − | − | + | + | * | − | Xqter-Xp11:14q32-14qter |
| RAG GO 4 | + | + | − | * | + | + | − | * | − | − | − | − | − | + | + | + | − | − | − | − | − | + | − | + | − | 6pter-6q13 |
| RAG SU 3-1-2-3 | − | − | + | * | − | − | + | − | * | − | − | − | − | − | − | − | − | + | + | − | − | + | + | + | − | 3qter-3p14:17q23-17qter |
| A9 SU 1-2 | + | + | − | + | + | − | + | − | − | − | + | + | + | − | + | − | − | + | − | − | − | + | + | + | + | |
| V79 HY 3-2 | + | + | − | + | + | − | − | + | + | − | + | − | + | − | + | + | − | − | − | − | − | + | + | + | + | |
| V79 HY 3-3 | − | − | − | − | − | − | − | − | − | − | − | − | − | − | − | − | − | + | − | − | * | + | + | − | − | Xpter-Xq22:19q133-19qter |
| CH.HAMSTER.P3 | + | + | − | + | + | − | − | + | − | − | − | + | − | − | * | + | + | + | − | − | − | − | + | * | − | Xq13-Xqter:14pter-14q32 |
| A9 GM89 9-C | + | + | * | − | + | − | − | − | − | − | − | − | − | + | + | − | − | − | − | − | − | − | + | * | − | 1pter-1q12:Xq26-Xqter |
| RAG GM97-8-13 | + | * | − | − | + | − | − | − | − | + | − | − | − | − | + | − | − | − | − | − | − | − | − | * | − | |
| MOUSE RAG | − | − | − | − | − | − | − | − | − | − | − | − | − | − | − | − | − | − | − | − | − | − | − | − | − | |

+Entire Chromosome
*Marker Chromosome

Deposit of Microorganisms

Many polynucleotide sequences may be used to practice the present invention. Exemplary of such sequences are human genomic sequences which have been cloned into recombinant plasmids designated pAC400, and pAC407. FIGS. 3A–3B show the relationships among the cloned sequences of this invention.

*E. coli* (strain HB101) carrying plasmids pAC400 and pAC407 have been deposited with the Agricultural Research Culture Collection (NRRL), Peoria, Ill., on Jan. 25, 1991, and have been assigned accession numbers NRRL B-18761 and B-18762, respectively.

The subject cultures have been deposited under conditions that assure that access to the cultures will be available during the pendency of this patent application to one determined by the Commissioner of Patents and Trademarks to be entitled thereto under 37 CFR 1.14 and 35 U. S. C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

*E. coli* HB101 is available from the NRRL repository where its accession number is NRRL B-11371. Plasmids can be isolated from the *E. coli* host by use of standard procedures, e.g., using cleared lysate-isopycnic density gradient procedures, and the like.

The present invention is not to be limited in scope by the microorganisms deposited, since the deposited embodiment is intended as a single illustration of one aspect of the invention. Many variations of this invention as herein set forth may be made without departing from the spirit and scope thereof. The specific embodiments described are given by way of example only, and the invention is limited only by the terms of the appended claims.

---

---

We claim:

1. A polynucleotide sequence comprising an insert of plasmid pAC400, wherein said insert hybridizes to and detects polymorphism at human DNA locus D4S 163 under hybridization conditions of 65° C. in 5×SSPE, 1 to about 2% SDS, and 0.5 to 1 mg/ml heparin.

2. A polynucleotide sequence comprising an insert of plasmid pAC407, wherein said insert hybridizes to and detects polymorphism at human DNA locus D4S163 under hybridization conditions of 65° C. in 5×SSPE, 1 to 2% SDS, and 0.5 to 1 mg/ml heparin.

3. A polynucleotide sequence substantially homologous to one or both flanking regions of a VTR fragment of pAC400 or pAC407, wherein said substantial homology is greater than 50% to enable hybridization to and detection of human DNA locus D4S163 under hybridization conditions of 65° C. in 5×SSPE, 1 to 2% SDS, and 0.5 to 1 mg/ml heparin.

* * * * *

UNITED STATES PATENT AND TRADEMARK OFFICE
CERTIFICATE OF CORRECTION

PATENT NO. : 5,514,547

DATED : May 7, 1996

INVENTOR(S) : Balazs et al.

It is certified that error appears in the above-identified patent and that said Letters Patent is hereby corrected as shown below:

Column 7: Line 59: ". complementarity" should read --complementarity--.

Column 11: Line 46: "Sinai" should read --SmaI--.

Signed and Sealed this

Twentieth Day of August, 1996

Attest:

BRUCE LEHMAN

*Attesting Officer*    *Commissioner of Patents and Trademarks*